(12) United States Patent
Smith et al.

(10) Patent No.: US 7,091,369 B2
(45) Date of Patent: Aug. 15, 2006

(54) SYNTHESIS OF POLYCONJUGATED FATTY ACIDS

(75) Inventors: William Smith, Ann Arbor, MI (US); Dmitry V. Kuklev, Ypsilanti, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 70 days.

(21) Appl. No.: 10/819,651

(22) Filed: Apr. 7, 2004

(65) Prior Publication Data

US 2005/0014826 A1    Jan. 20, 2005

Related U.S. Application Data

(60) Provisional application No. 60/487,892, filed on Jul. 15, 2003.

(51) Int. Cl.
C07C 57/00    (2006.01)

(52) U.S. Cl. ................ 554/224; 554/126; 554/223; 554/227

(58) Field of Classification Search ............ 554/224, 554/126, 223, 227
See application file for complete search history.

(56) References Cited

U.S. PATENT DOCUMENTS

| | | |
|---|---|---|
| 5,855,917 A | 1/1999 | Cook et al. |
| 6,160,141 A | 12/2000 | Seidel |
| 6,245,811 B1 * | 6/2001 | Horrobin et al. ........... 554/224 |
| 6,342,619 B1 | 1/2002 | Seidel |
| 6,479,683 B1 | 11/2002 | Abney et al. |

2001/0049451 A1    12/2001    Seidel

OTHER PUBLICATIONS

Sklar et al., Proc Natl Acad Sci U S A 1975, 72, 1649-1653.
Sklar et al., Biochemistry 1977, 16, 819-828.
Sklar et al., Biochemistry 1977, 16, 813-819.
Sklar et al., Biochemistry 1977, 16, 5100-8.
Sklar et al., Biochemistry 1979, 18, 1707-16.
Narayanaswami et al., Biochemistry 1993, 32, 12420-7.
Brewer and Matinyan, Biochemistry 1992, 31, 1816-20).
Ben-Yashar and Barenholz, Chem Phys Lipids 1991, 60, 1-14.
Hubbel and Altenbach, C. (1994) In Membrane protein structure: experimental approaches (Ed, White, S. H.) Oxford University Press, New York, pp. 224-248.
Kasurinen et al., Biochemistry 1990, 29, 8548-54.
Suzuki et al., Biochemistry 1993, 32, 10692-9.
Tribble et al., PNAS 1994, 91, 1183-1187.
Crook et al., Cell 1994, 79, 817-27.
Hockenbery et al., Cell 1993, 75, 241-51.
Corey, E. J. et al. (1983) Proc Natl Acad Sci U S A 80(12):3581-3584.
Kuklev, D. V. et al. (1991) Bioorganicheskaya Khimiya 17(11):1574-1581.
Kuklev, D. V. et al. (1992). Phytochemistry 31:2401-2403.
Kuklev, D. V. et al. (1997) Chemistry and Physics of Lipids 85:125-134.
Kuklev, D. V. et al. (1996) Bioorganicheskaya Khimiya 22:622-627.
Kuklev, D. V., and W. L. Smith (2003) J. Lipid. Res. 44:1060-1066.
Camps et al. (1999) Sheffield Academic Press 94-126.

(Continued)

*Primary Examiner*—Deborah D. Carr
(74) *Attorney, Agent, or Firm*—Medlen & Carroll, LLP

(57) ABSTRACT

The present invention relates to fatty acids. In particular, the present invention provides polyconjugated fatty acids, and methods of their synthesis and their use.

20 Claims, 9 Drawing Sheets

OTHER PUBLICATIONS

Kuklev, D. V., and V. V. Bezuglov (1994) Bioorganicheskaya Khimiya 20:341-366.
Young, D. C. et al. (1990) J. Chromatogr. 522:295-302.
Lopez A. and Gerwick W.H. (1987) Lipids vol. 22, No. 3, pp. 190-194.
Michailova M. V. et al. (1995) Lipids 30 (7): 583-589.
Wise M.L. et al. (1994) Biochemistry 33: 15223-15232.
Souto et al. (1994) Tetrahedron Letters 35:5907-5910.
Wright, S. W. et al. (1987) J. Org. Chem. 52(19):4399-4301.
Corey, E. J. et al. (1980) J. Am. Chem. Soc. 102(4):1435-1436.
Johnson, R. W., and E. H. Pryde (1979) In Fatty Acids (E. H. Pryde, editor; American Chemical Society, Champaign, III) 319-342.
Frankel, E. N. (1979) In Fatty Acids (E. H. Pryde, editor; American Chemical Society, Champaign, III) 426-456.
Johnson, R. W (1979). In Fatty Acids (E. H. Pryde, editor; American Chemical Society, Cahmpaign, III) 342-352.

* cited by examiner a        b

SYNTHESIS OF POLYCONJUGATED FATTY ACIDS

This application claims priority to provisional patent application Ser. No. 60/487,892, filed Jul. 15, 2003, which is herein incorporated by reference in its entirety.

The present application was funded in part with government support under grant number DK22042 from the National Institutes of Health. The government may have certain rights in this invention.

FIELD OF THE INVENTION

The present invention relates to fatty acids. In particular, the present invention provides polyconjugated fatty acids, and methods of their synthesis and their use.

BACKGROUND OF THE INVENTION

Fatty acids with conjugated double bonds are well known naturally occurring compounds. Most fatty acids or fatty acid derivatives are single chain hydrocarbon molecules, with from 3 to up to 22 or more carbons. Many naturally occurring fatty acids are unsaturated, which means that they have at least one double bond; a fatty acid with two or more double bonds is referred to as polyunsaturated fatty acid. (The presence of a single double bond results in an enyne, two in a diene, three in a triene, four in a tetraene, five in a pentaene, six in a hexaene, seven in a heptaene, etc.) Most double bonds in polyunsaturated fatty acids are unconjugated polyenes, or methylene-interrupted polyenes, in that the double bonds are separated by a methyl group. However, in fewer cases, double bonds are conjugated, in that two double bonds are separated only by a single bond. Among naturally occurring conjugated polyenes, conjugated dienes and trienes are the most prevalent. Each conjugated double bond can exist in one of two isomeric forms: cis (referred to as c or Z), or trans (referred to as t or E).

Conjugated fatty acids have numerous commercial utilities. One is in drying oils. Drying oils are of value due to their ability to polymerize or dry after application to a surface to form tough, adherent and abrasion-resistant films. Upon exposure to oxygen, unconjugated polyenes, such as those contained in linseed oil and tung oil, oxidize and cross-link to form such films; however, conjugated polyenes cross-link more rapidly, are thus valued by the paint and varnish industries for use in drying oils.

Another utility is in the area of health and nutrition. Research has shown that conjugated polyenes may inhibit tumor growth, prevent heart disease, and reduce body fat. For example, investigations of the biological activity of conjugated fatty acids have suggested that they possess anti-arteriosclerosis effects, boost the immune system, and affect energy metabolism, promoting protein deposition while decreasing fat deposition. Yet another use is the presence of conjugated fatty acids in many insect pheromone blends.

Yet another utility is as research reagents. Long chain conjugated polyenes can be both fluorescent and photoreactive, and thus useful as probes or markers. For example, parinaric acid, a naturally occurring polyconjugated fatty acid, has been utilized as a fluorescent membrane probe to detect phase transitions in bilayers as well as interactions between lipids and proteins. Parinaric acid can be biosynthetically incorporated into phospholipids, and its environment examined thorough spectroscopic characterization. Additional information about the dynamics of membrane behavior as well as interactions between proteins and lipids can be obtained by using other conjugated double bond systems (e.g., with the chromophore in the middle of the fatty acid or near the carboxyl group (Goerger M. M. and Hudson B. S. (1988) *J. Org. Chem.* Vol. 53, No. 14, pp. 3148–3153). It appears that both the number and location of the conjugated double bonds within the fatty acid chain can affect the utility of the molecule as a research probe.

Although some polyconjugated fatty acids are naturally occurring (for example, several examples have been identified in marine plants), these fatty acids occur in limited quantities and in limited conformations. Thus, there is a need to develop other polyconjugated fatty acids with different conformations. There is also a need to provide other polyconjugated fatty acids in sufficient quantities to use as research tools, and potentially to use as nutritional supplements or as drugs or as platforms for developing drugs.

Although some methods exist to prepare conjugated polyenes, investigators continue to seek more efficient methods, as well as methods which can manipulate either the number and/or the location of the conjugated double bonds within a single fatty acid or fatty acid derivative. Moreover, methods are also sought which control the isomeric form of each conjugated double bond.

SUMMARY OF THE INVENTION

Thus, the present invention provides novel directed chemical synthetic methods for the preparation of a polyconjugated system of double bonds close to carboxyl end of the methylene interrupted system of double bonds in natural polyunsaturated fatty acids. The present invention also provides novel polyconjugated fatty acid products.

Thus, in some embodiments, the present invention provides a composition comprising a polyconjugated fatty acid, wherein the polyconjugated fatty acid is selected from the group consisting of 5E,7E,9E,11Z,14Z- and 5E,7E,11E,14Z eicosapentaenoic acid, 5E,7E,9E,11Z,14Z,17Z- and 5E,7E,9E,11E,14Z,17Z-eicosahexaenoic acid, and 4E,6E,8E,10Z,13Z,16Z,19Z- and 4E,6E,8E,10E,13Z,16Z,19Z -docosaheptaenoic acid. In other embodiments, the present invention provides a composition comprising an ester of a polyconjugated fatty acid, wherein the polyconjugated fatty acid is selected from the group consisting of 5E,7E,9E,11Z,14Z- and 5E,7E,11E,14Z eicosapentaenoic acid, 5E,7E,9E,11Z,14Z,17Z- and 5E,7E,9E,11E,14Z,17Z-eicosahexaenoic acid, and 4E,6E,8E,10Z,13Z,16Z,19Z- and 4E,6E,8E,10E,13Z,16Z,19Z -docosaheptaenoic acid. In some further embodiments, the ester is selected from the group consisting of a methyl ester and an ethyl ester.

In other embodiments, the present invention provides a composition comprising a lipid comprising at least one polyconjugated fatty acid, wherein the polyconjugated fatty acid is selected from the group consisting of 5E,7E,9E,11Z,14Z- and 5E,7E,11E,14Z eicosapentaenoic acid, 5E,7E,9E,11Z,14Z,17Z- and 5E,7E,9E,11E,14Z,17Z -eicoshexaenoic acid, and 4E,6E,8E,10Z,13Z,16Z,19Z- and 4E,6E,8E,10E,13Z,16Z,19Z-docosaheptaenoic acid. In some further embodiments, the lipid is a glycerolipid. In some yet further embodiments, the glycerolipid is a triglyceride, a diglyceride, a monoglyceride, a phospholipid, a lysophospholipid, a glycolipid, or a lysoglycolipid.

In other embodiments, the present invention provides a method of synthesizing a polyconjugated fatty acid product, comprising providing an iodolactone of a fatty acid dissolved in dry benzene, wherein the fatty acid is arachidonic, eicosapentaenoic, or eicosahexaenoic acid, and reacting the fatty acid iodolactone with dry DBU. In some further embodiments, the fatty acid iodolactone is reacted with a molar excess of dry DBU, forming a polyconjugated fatty acid product. In other further embodiments, the fatty acid iodolactone is reacted with an about equimolar amount of dry DBU, forming an allylic lactone of the fatty acid, and the method further reacting the allylic lactone of the fatty acid with a molar excess of DBU.

In other further embodiments, the fatty acid iodolactone is reacted with an about equimolar amount of DBU, forming an allylic lactone of the fatty acid, and the method further comprises reacting the allylic lactone of the fatty acid with base to form a hydroxy fatty acid product, reacting the hydroxy acid product with chlorotrimethylsilane to form a trimethylsilylether of the methyl ester of the hydroxy acid, and reacting the trimethylsilylether of the methyl ester of the hydroxy acid product with acid to form a methyl ester of a polyconjugated fatty acid product.

In yet other embodiments, the fatty acid iodolactone is reacted with an about equimolar amount of DBU, forming an allylic lactone of the fatty acid, and the method further comprises reacting the allylic lactone of the fatty acid with acid to form a methyl ester of a polyconjugated fatty acid product.

In other embodiments, the present invention provides a method of synthesizing a polyconjugated fatty acid product, comprising providing an iodolactone of a fatty acid, wherein the fatty acid is arachidonic, eicosapentaenoic, or eicosahexaenoic acid, reacting the fatty acid iodolactone with triethylamine to form a methyl ester of an epoxy fatty acid, reacting the methyl ester of an epoxy fatty acid with actylbromide to form a bromoacetate, and reacting the bromoacetate with dry DBU in dry benzene to form a methyl ester of a polyconjugated fatty acid.

In yet other embodiments, the present invention provides a method of synthesizing a polyconjugated fatty acid product, comprising providing a trimethylsilyl ether of an allylic alcohol, where the allylic alcohol is 5-HETE, 5-HEPE, or 4-HDHE, and treating the trimethylsilyl ether of an allylic alcohol with aqueous hydrochloric or trifluoracetic acid.

In other embodiments, the present invention provides a method of purifying polyconjugated fatty acid products, comprising providing a polyconjugated fatty acid product in a solvent adding a high boiling solvent, evaporating the solvent in which a polyconjugated fatty acid product is dissolved, dissolving the residual polyconjugated fatty acid product in a water/alcohol/acid solution, and isolating the polyconjugated fatty acid product by solid phase extraction chromatography. In further embodiments, the method further comprises concentrating and purifying the polyconjugated fatty acid by HPLC. In yet further embodiments, the method further comprising crystallizing the polyconjugated fatty acid at very low temperatures. In some embodiments of the method, the polyconjugated fatty acid product is a polyconjugated fatty acid or an ester of a polyconjugated fatty acid. In other embodiments of the method, the high boiling solvent is dry diglyme, triglyme, tetraglyme or DMSO.

In other embodiments, the present invention provides a method of synthesizing a polyconjugated fatty acid product, comprising providing an iodolactone of a fatty acid dissolved in dry benzene, wherein the fatty acid is arachidonic, eicosapentaenoic, or eicosahexaenoic acid, and reacting the fatty acid iodolactone with dry DBU, where a polyconjugated fatty acid product is synthesized on a preparative scale. In other embodiments, the present invention provides a method of synthesizing a polyconjugated fatty acid product, comprising providing an iodolactone of a fatty acid dissolved in dry benzene, wherein the fatty acid is arachidonic, eicosapentaenoic, or eicosahexaenoic acid, and reacting the fatty acid iodolactone with dry DBU, where a polyconjugated fatty acid product is synthesized in a high yield. In yet further embodiments of the method, a polyconjugated fatty acid product is synthesized on a preparative scale of at least about 100 mg, and in high yield of at least about 50%.

In other embodiments, the present invention provides a method of synthesizing a polyconjugated fatty acid product, comprising providing an iodolactone of a highly unsaturated fatty acid dissolved in dry benzene, wherein the highly unsaturated fatty acid comprises at least three methylene interrupted double bonds where the position of the first double bond of the at least three methylene interrupted double bonds is from delta-3 to delta-5 position of the carbon chain, and reacting the fatty acid iodolactone with dry DBU. In further embodiments, the fatty acid iodolactone is reacted with a molar excess of dry DBU, forming a polyconjugated fatty acid product. In some embodiments, the present invention provides a polyconjugated fatty acid product synthesized by the method.

In still further embodiments, the present invention provides a composition comprising a polyconjugated fatty acid, wherein the polyconjugated fatty acid is 9Z,11E,13E,15E-octadecatetraenoic acid.

In yet other embodiments, the present invention provides a method of synthesizing parinaric acid isomers, comprising reacting a free fatty acid, wherein the free fatty acid is alpha-linolenic acid, with bromine to produce a vicinal-dibromide of the alpha-linolenic acid; and reacting the vicinal-dibromide with DBU to generate parinaric acid isomers. In some embodiments, the free fatty acid is derived from an oil by a method comprising the steps of dissolving the oil in a boiling ethanolic solution of potassium hydroxide to generate a reaction solution; boiling the reaction solution under reflex; acidifying the reaction solution; extracting the organic layer from the reaction solution; and drying the organic layer to generate free fatty acids. In some embodiments, the method further comprises the step of enriching the free fatty acids for alpha-linolenic acid. In some further embodiments, the method further comprises the step of purifying the parinaric acid isomers.

DESCRIPTION OF THE FIGURES

A) 5E,7E,9E,11Z,14Z-eicosapentaenoic acid
B) 5E,7E,9E,11E,14Z-eicosapentaenoic acid
C) 5E,7E,9E,11Z,14Z,17Z-eicosahexaenoic acid
D) 5E,7E,9E,11E,14Z,17Z-eicosahexaenoic acid
E) 4E,6E,8E,10Z,13Z,16Z,19Z-docosaheptaenoic acid
F) 4E,6E,8E,10E,13Z,16Z,19Z-docosaheptaenoic acid

DEFINITIONS

Figure 1:
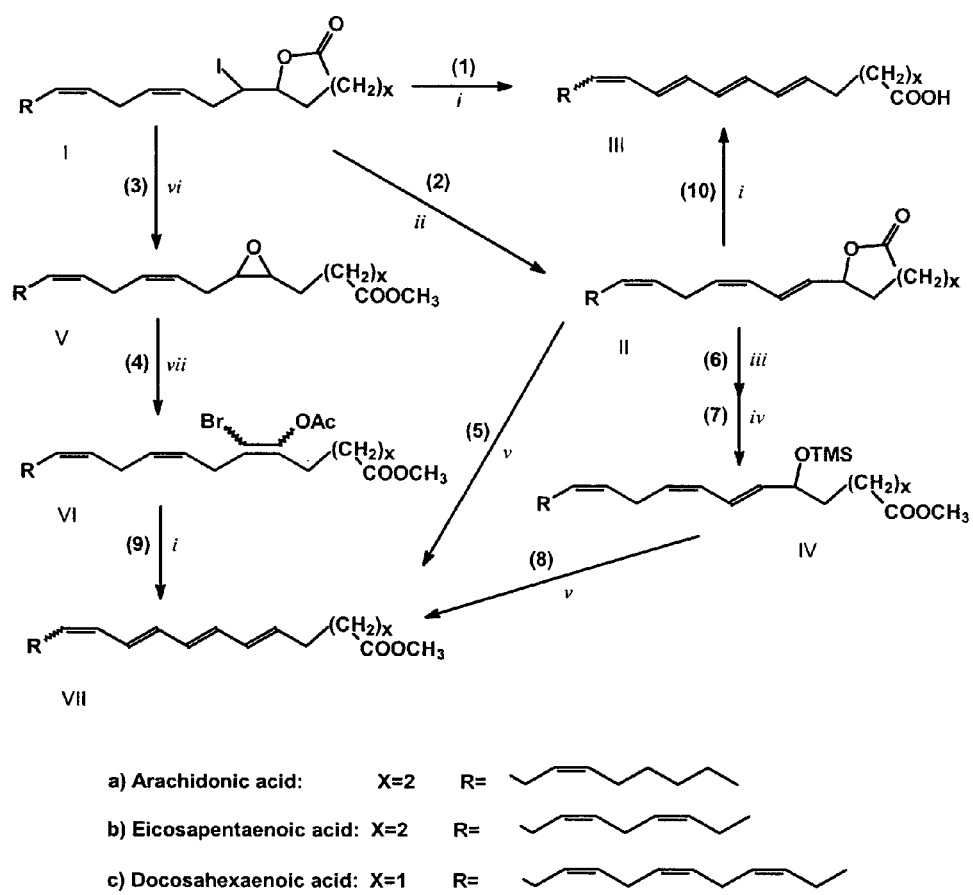
FIG. 1 shows the formation of polyconjugated fatty acids from natural polyunsaturated fatty acids. Reagents and conditions: (i) 2.2 mol DBU, 72 hr, 24° C.; (ii) 1.1 mol DBU, 12 hr, 24° C.; (iii) 0.2 N KOH, 40% EtOH, 16 hrs, 24° C.; (iv) $CH_2N_2$/ether; chlorotrimethylsilane/pyridine, 1 hr, 70° C.; (v) 0.5% $H_2SO_4$ in methanol in a sealed ampule, 80° C., 1 hr; (vi) 3 mol triethylamine in methanol, boiling under reflux, 5 hr, (vii) 1.15 mol AcBr in ether, 1 hr, 24° C.

To facilitate an understanding of the present invention, a number of terms and phrases as used herein are defined below:

As used herein, the term "unsaturated" when used in reference to a fatty acid refers to the presence of at least one double bond in the fatty acid. Most double bonds in polyunsaturated fatty acids are unconjugated polyenes, or methylene-interrupted polyenes, in that the double bonds are separated by a methyl group.

As used herein, the term "polyunsaturated" when used in reference to a fatty acid refers to the presence of two or more double bonds in a fatty acid.

As used herein, the term "highly unsaturated" when used in reference to a fatty acid refers to the presence of three or more double bonds in a fatty acid.

As used herein, the term "conjugated" when used in reference to an unsaturated fatty acid refers to two double bonds separated only by a single bond in a fatty acid.

As used herein, the term "polyconjugated" when used in reference to an unsaturated fatty acid refers to a system of three or more conjugated double bonds, where each double bond in the system is separated from other double bonds in the system by only a single bond.

As used herein, the term "polyconjugated fatty acid product" refers to a product of a reaction or series of reactions in which a starting reactant is a highly unsaturated fatty acid and a product of the reaction or series of reactions is a molecule with a polyconjugated double bond system; typically, such products are polyconjugated fatty acids or the methyl esters of polyconjugated fatty acids.

As used herein, the term "diglyme" refers to 2-methoxyethyl ether.

As used herein, the term "dry" when used in reference to a solvent or a reagent refers to the solvent or reagent from which small quantities of water have been removed, by chemical or physical means.

As used herein, the term "equimolar" when used in reference to DBU in a chemical reaction mixture refers to the presence of about the same molar amount of DBU as a second reactant in the chemical reaction; about the same means a range from about 0.8 to about 1.2 times the molar amount of the second reactant.

As used herein, the term "molar excess" when used in reference to DBU in a chemical reaction mixture refers to the presence of a greater molar amount of DBU than a second reactant in the chemical reaction; a greater amount means greater than at least about 1.2 times the molar amount of the second reactant.

As used herein, the term "lipid" includes a substance that is insoluble in water, is soluble in organic solvents, such as chloroform, ether or benzene, and contains long chain hydrocarbon groups in the molecules. Typically, lipids are present in or derived from living organisms. Lipids include simple lipids and complex lipids. Simple lipids include glycerides (including triacylglycerols or triglycerides, diacylglycerols or diglycerides, and monoacylglycerols or monoglycerides), alkyl-diacylglycerols and neutral plasmalogens, and cholesterol and cholesterol esters. Complex lipids include glycerophospholipids or phosphoglycerides, glycoglycerolipids or glycosyldiglycerides, and sphingolipids.

As used herein, the term "glycerolipid" refers to lipids with a three carbon backbone, typically derived from glycerol. A glycerolipid includes glycerides, phospholipids (glycerophospholipids), and glycolipids (glycoglycerolipids). A phospholipid or glycolipid that contains only one fatty acid or acyl group is referred to as a "lysolipid," for example, a lysophospholipid or lysoglycolipid.

As used herein, the term "preparative scale" when used in reference to synthesis of a polyconjugated fatty acid product means in an amount sufficient to be useful for subsequent analysis and/or use. Typically, such an amount is at least about 10 mg; in other embodiments, such an amount is at least about 25 mg; in yet other embodiments, such an amount is at least about 50 mg; and in yet other embodiments, such an amount is at least about 100 mg.

As used herein, the term "high yield" when used in reference to synthesis of a polyconjugated fatty acid product means in a yield of at least about 10%; in other embodiments, a high yield is at least about 25%; in yet other embodiments, a high yield is at least about 50%.

As used herein, the term "at very low temperature" when used in reference to storage or crystallization of a polyconjugated fatty acid product refers to at least about minus 20° C.; in other embodiments, it refers to at least about minus 40° C.; in yet other embodiments, it refers to at least about minus 60° C.; and in yet other embodiments, it refers to at least about minus 80° C.

DESCRIPTION OF THE INVENTION

The present invention relates to fatty acids. In particular, the present invention provides polyconjugated fatty acids, and methods of their synthesis and their use.

Thus, methods of the present invention can be used to prepare photoactive derivatives of n-3 and n-6 highly unsaturated fatty acids (HUFAs). These photoactive derivatives can then be employed in various capacities, including but not limited, as probes for defining further the biological functions of essential fatty acids.

In some particular embodiments, the present invention provides a novel method for the synthesis of isomers of parinaric acids from α-linoleic acid. The present invention further provides novel isomers of parinaric acid (e.g., synthesized by the methods of the present invention).

Compounds

The present invention provides methods of preparing polyunsaturated fatty acids with the relatively stable conjugated tetraenoic system, as well as novel fatty acid intermediates and products comprising the conjugated tetraenoic system. These products comprise fatty acids bearing a photoreactive conjugated tetraene group near the carboxyl group and a natural methylene interrupted n-3 or n-6 grouping. In some embodiments, fatty acids of the n-3 and n-6 families containing a photoactive conjugated tetraene group near the carboxylate were prepared from several naturally occurring fatty acids by iodolactonization followed by treatment with excess 1,8-diazobicyclo[5.4.0]unec-7-ene. The new conjugated fatty acids include 5E,7E,9E,11Z,14Z- and 5E,7E,9E,11E,14Z -eicosapentaenoic acids derived from arachidonic acid (AA); 5E,7E,9E,11Z,14Z,17Z- and 5E,7E, 9E,11E,14Z,17Z-eicosahexaenoic acids from eicosapentaenoic acid (EPA); and 4E,6E,8E,10Z,13Z,16Z,19Z- and 4E,6E,8E,10E,13Z,16Z,19Z -docosaheptaenoic acids from docosahexaenoic acid DHA). All of the newly synthesized fatty acids were characterized by UV, $^1$H-NMR and mass spectroscopy. These new products represent the first examples of directed transformations of methylene interrupted double bond systems. The products can be synthesized on a preparative scale (greater than about 100 mg) and in high yields (greater than about 50%).

Thus, the methods of the present invention resulted in the first successful synthesis in a high yield and in a preparative scale of a novel set of polyconjugated and polyunsaturated fatty acids which contain a system of four conjugated double bonds and from one to three double bonds with their natural cis-configuration and at ω-3/ω-6 position. The novel fatty acids of the present invention have pronounced spectral properties that are quite different from those of natural fatty acids, and that allow identification of them in fatty acids mixtures, and in model and biological membranes.

Naturally occurring fatty acids with a conjugated triene system linked to a system of methylene interrupted double bonds have not been reported. Furthermore, fatty acids with a conjugated triene system were not observed as reaction products in the synthetic methods of the present invention. The results of these methods, described below and in the Examples, indicate that it is not possible to introduce a triene structure neighboring a methylene interrupted system of double bonds; instead the apparently more stable conjugated tetraene system forms spontaneously. This occurs independently of the position of the most carboxyl proximal double bond and of the length of the methylene interrupted double bond system. Formation of the tetraene is also independent of the nature of the reagents (e.g. acidic vs. basic). The location of the conjugated double bond system remains the same as the position of the first double bond in the parent fatty acid (e.g. the 5,8,11 methylene interrupted system of AA (C-5 to C-12) converts to the conjugated 5,7,9,11 system (C-5 to C-12). Furthermore, naturally occurring fatty acids with a conjugated triene system linked to a system of methylene interrupted double bonds have not been reported.

Taken together, the lack of any reported naturally occurring and of any observed synthetic and conjugated triene system linked to a system of methylene interrupted double bonds lead to a conclusion conclude that this type of structure is unstable and cannot exist in nature. The conjugated tetraene system was synthesized and characterized by the methods of the present invention; the conjugated tetraene system, in contrast to the conjugated triene system, is quite stable in the form of E,E,E,Z-system, before undergoing a slow spontaenous isomerization to a E,E,E,E-system. This rearrangement has not been described previously.

The present invention also comprises lipids comprising at least one polyconjugated fatty acid described above. In some embodiments, the lipids comprising at least one polyconjugated fatty acid are glycerolipids. The lipids may be synthesized in vivo, as for example, from the addition of a polyconjugated fatty acid as described above to a cell, or they may be synthesized in vitro, as for example by the addition of a polyconjugated fatty acid as described above to a reaction mixture comprising an appropriate lipid substrate and lipid synthesizing enzyme. Appropriate lipid substrates and lipid synthesizing enzymes include subcellular fractions comprising membrane micelles, which include either or both the substrate and the enzyme. Lipid substrates and lipid synthesizing enzymes, as well as techniques to synthesize lipids from a suitable substrate and a polyconjugated fatty acid of the present invention, are well known (see, for example, Biochemistry of Lipids, Lipoproteins, and Membranes, 4$^{th}$ Ed. (2002; Vance D E and Vance, J E, editors; Elsevier, Amsterdam, Boston); Enzymes in Lipid Modification (2000; Bornsheuer, U T, editor; Wiley-VCH, Weinheim, N.Y.); Lipid Synthesis and Manufacture (1999; Gunstone, F D, editor; Sheffield Academic Press, Sheffield, England; CRC Press, Boca Raton, Fla.); Lipid Biochemistry, 5$^{th}$ Ed (2002; Gurr, M I, Harwood, J L, and Frayn, K N, editors; Blackwell Science, Oxford, Malden, Mass.). Exemplary suitable substrates include but are not limited to glycerol-3-phospate, lysopholipids, lysoglycolipids, and mono- and diglycerides, and exemplary suitable enzymes include but are not limited to various acyl transferases and lipases. Lipids comprising at least one polyconjugated fatty acid described above can be further isolated by well known methods (see, for example, references cited above), modified as described below to avoid polymerization of the polyconjugated fatty acids.

The present invention further provides conjugated tetraenes of octadecanoic acid (e.g., octadecatetraenoic acid). For example, in some embodiments, the present invention provides α-parinaric acid (9Z,11E,13E,15Z-octadecatetraenoic acid), 9E,11E,13E,15Z -octadecatetraenoic acid, 9E,11E,13E,15Z-octadecatetraenoic acid, and β-parinaric acid (9E,11E,13E,15E-octadecatetraenoic acid).

Methods

Naturally occurring highly unsaturated fatty acid (HUFAs) can be used as starting materials to develop photosensitive conjugated tetraenes systems neighboring the carboxyl groups. It is contemplated that a HUFA substrate, to be converted to a polyconjugated fatty acid product of the present invention, comprises at least three methylene interrupted double bonds (to form a tetraenoic conjugated system by the methods of the present invention), where the position of the first double bond of the methylene interrupted system is from delta-3 to delta-5 position of the carbon chain (to form an iodolactone by the methods described further below. Although it is not necessary to understand the mechanism to practice the invention, and the invention is not intended to be limited to any particular mechanism, it is contemplated that the iodolactone product is a key intermediate in the reactions of the present invention, as it allows use of the carboxylic function of the fatty acid substrate to choose one double bond, the one closest to the carboxylic function, to modify the last one from others).

These HUFAs are subjected to iodolactonization of the carboxyl group followed by treatment with 1,8-diazobicyclo [5.4.0]undec-7-ene (DBU) (FIG. 1). The iodolactone can be reacted directly with DBU; depending upon the relative amount of DBU used, the products of the reaction are either polyconjugated fatty acids (when excess amounts of DBU are used) or an allylic lactone (when about equimolar amounts of DBU are used). Allylic lactones can be converted to methyl esters of the polyconjugated fatty acids by one of two routes. One is by base cleavage of the allylic lactone ring, forming hydroxy fatty acids, which can then be converted to a trimethylsilylether of the methyl ester, which in turn is converted to a polyconjugated fatty acid methyl ester. Another route is by acidic cleavage of the allylic lactone ring, resulting in the formation of a polyconjugated fatty acid methyl ester. Alternatively, iodolactones can be used to produce polyconjugated fatty acid methyl esters in a series of reactions, in which the last reaction involves DBU. In these reactions, the iodolactone is converted to an epoxide methyl ester, which is then converted by an epoxide ring opening to a bromoacetate, which can then be reacted with DBU to form the polyconjugated fatty acid methyl ester product.

The iodolactonization protocol is mild and provides for regioselective modification of the double bond closest to the carboxyl group of HUFAs in high yield while leaving other double bonds intact (Solodovnik, V. D. (1967) Russian Chemical Reviews 36:272–283; and Kuklev, D. V. and V. V. Bezuglov (1994) Bioorganicheskaya Khimiya 20:341–366). Iodolactonization comprises dissolving a HUFA in a solvent (in particular embodiments, the solvent is ethanol; in more particular embodiments, $KHCO_3$ in water is added. KHCO3 is used to form salts from the fatty acid substrates, where it is contemplated that iodolactonization results in higher yields). $I_2$ in a solvent is then added to the solution of HUFA (in particular embodiments, $I_2$ is added in ethanol, and then hexane is also added to the reaction mixture; it is contemplated that the iodolactones accumulate in the upper hexane layer, and the presence of a two phase reaction mixture results in higher yields). The reaction mixture is incubated for a period of time sufficient to produce an iodolactone of the HUFA; the iodolactones are then extracted into a second solvent (in particular embodiments, the second solvent is hexane). The solvents containing the iodolactones are then preferably washed with aqueous solutions, and then the solvent is removed, preferably under a vacuum. The oily residue of HUFA iodolactones are redissolved in a solvent, and preferably an anti-oxidant is added to the solution; the HUFA iodolactone is then stored at very cold temperatures, preferably at about –80° C. The individual iodolactones can then be isolated, for example by column chromatography. Exemplary but non-limiting methods of iodolactonization are provided in Example 2. Exemplary products are γ-iodolactone of DHA, δ-iodolactone of EPA, and δ-iodolactone of AA, as shown in FIG. 1.

In some embodiments, the present invention provides methods for the creation of a conjugated system of double bonds by reacting an iodolactone prepared from a HUFA with DBU, where DBU is used in about equimolar amounts with the iodolactone; the product of the reaction is the corresponding lactone of the allylic alcohol. Typically, the methods comprise providing an iodolactone dissolved in a solvent, to which an about equimolar amount of DBU in the same solvent is added; in particular embodiments, the solvent is dry benzene. The reaction mixture is incubated in the dark under an inert atmosphere at about room temperature for a time sufficient to result in production of an allylic lactone product. The product precipitates from the solvent, and can be separated from the solvent, as for example by centrifugation or by filtration. The separated product is typically redissolved in a solvent, and in particular embodiments the same solvent in which the reaction occurred, to which preferably an anti-oxidant (for example, BHT) is added. In further embodiments, the allylic lactone product is purified, in particular embodiments by column chromatography (for example, a silica gel column); in particular embodiments, the product is purified using a gradient of dry ether in dry benzene. Exemplary methods are provided in Example 2. Exemplary products include γ-lactone of 4-HDHE (4-hydroxy, 5E,7Z,11Z,13Z,16Z,19Z-docosahexaenoic acid) from γ-iodolactone of DHA, δ-lactone of 5-HEPE (5-hydroxy,6E,8Z,11Z,14Z,17Z-eicosapentaenoic acid) from δ-iodolactone of EPA, and δ-lactone of 5-HETE (5-hydroxy,6E,8Z,11Z,14Z-eicosatetraenoic acid) from δ-iodolactone of EPA, as shown in FIG. 1.

Allylic lactones can be converted to methyl esters of the polyconjugated fatty acids by one of two routes. One is by base cleavage of the allylic lactone ring, forming hydroxy fatty acids, which can then be converted to a trimethylsilylether of the methyl ester, which in turn is converted to a polyconjugated fatty acid methyl ester. In these embodiments, the allylic lactone is saponified by the action of an aqueous base; the product of the reaction is the corresponding hydroxyacid, structures of which are wide distributed among the products of oxidative metabolism of HUFAs (Wright, S. W. et al. (1987) J. Org. Chem. 52(19):4399–4301; and Corey, E. J. et al. (1980) J. Am. Chem. Soc. 102(4):1435–1436). Typically, the allylic lactone ring is dissolved in a solvent (in particular embodiments, the solvent is ethanol), and a base (in particular embodiments, the base is KOH) is added. The reaction mixture is incubated at about room temperature for a period of time sufficient to result in formation of hydroxyacid. In further embodiments, water is added to the reaction mixture, and the solution is acidified (in particular embodiments by the addition of HCL) and extracted (in particular embodiments with hexane-ether). In yet further embodiments, the organic extract is washed (in particular embodiments with water and then with a saturated solution of NaCl), and then dried (in particular embodiments over $Na_2SO_4$). In yet further embodiments, the dry extract is filtered and then evaporated under a vacuum. Exemplary methods are provided in Example 2. Exemplary products include 4-HDHE prepared from γ-lactone of 4-HDHE (4-hydroxy,5E,7Z,10Z,13Z,16Z,19Z-docosahexaenoic acid), 5-HEPE from δ-lactone of 5-HEPE (5-hydroxy,6E,8Z,11Z,14Z,17Z-eicosapentaenoic acid), and 5-HETE from δ-lactone of 5-HETE (5-hydroxy,6E,8Z,11Z,14Z-eicosatetraenoic acid), as shown in FIG. 1.

In further embodiments, hydroxy acids are converted corresponding polyconjugated fatty acids in a series of reactions. Hydroxy acids are converted to the corresponding methyl ester; in particular embodiments, methods of conversion include using diazomethane in ether. The methyl ester is then converted to the corresponding trimethylsilylether of the methyl ester; in particular embodiments, the methyl ester is provided in dry pyridine, and chlorotrimethylsilane is added; the reaction mixture is then incubated at elevated temperatures for a sufficient period of time to produce the corresponding trimethylsilylether of the methyl ester. In particular embodiments, the reaction mixture is incubated at about 70° C. for about 2 hr. In further embodiments, the solvents are evaporated (as for example under a stream of nitrogen); in yet further embodiments, the reside is dissolved in a solvent (as for example hexane), and filtered. Exemplary methods are provided in Example 2. Exemplary trimethylsilylethers of the methyl esters are shown in FIG. 1.

In other embodiments, methods of the present invention comprise treatment of treatment of trimethylsilylethers of allylic alcohols (5-HETE, 5-HEPE, 4-HDHE) with aqueous hydrochloric or trifluoroacetic acid. Surprisingly, these reactions lead to formation of the same conjugated tetraene group as those obtained directly from natural HUFAs as starting materials. Although it is not necessary to understand the underlying mechanism, and the invention is not limited to any particular mechanism, it thus appears that an intermediate lactone is not required for the formation of conjugated tetraenes.

In these embodiments, a trimethylsilylether of a methyl ester is converted to its corresponding polyconjugated fatty acid methyl ester. In some embodiments, a dry oil of the trimethylsilylether of a methyl ester is provided in a solution (in particular embodiments, the solvent comprises diglyme) to which an acidic solution is added (in particular embodiments, the acid solution comprises HCL). The reaction mixture is incubated in a sealed ampule at elevated temperatures for a period of time sufficient to produce the corresponding polyconjugated fatty acid methyl ester. In particular embodiments, the incubation is about 2 hrs at about 80° C. In further embodiments, the reaction mixture is dissolved in a second solvent (in particular, methylene chloride), and washed with aqueous solutions (in particular embodiments, with water and with a salt solution; even more particularly, the salt is NaCl, and the solution is saturated). In yet further embodiments, the washed product is dried, filtered, and stored at low temperatures; in particular embodiments, the product is dried over anhydrous $Na_2SO_4$ and stored at about −80° C. Exemplary methods are provided in Example 2. Exemplary polyconjugated fatty acid methyl esters are shown in FIG. 1.

In these embodiments, it was observed that the formation of the conjugated tetraenoic fragment does not depend on the iodolactone ring size, as it can be seen by comparison of the reactions of γ-iodolactone DHA (which has a five atom ring lactone ring), and δ-iodolactones of EPA and AA (each of which have a six atom lactone ring). Although it is not necessary to understand the underlying mechanism, and indeed the present invention is not limited to any particular mechanism or hypothesis, it is contemplated that for all of these substrates, the mechanism of the reaction includes a first stage of a formation of the corresponding lactone of the allylic alcohol, and a second stage of the ring opening.

Another route by which allylic lactones can be converted to methyl esters of the polyconjugated fatty acids is by acidic cleavage of the allylic lactone ring, resulting in the formation of a polyconjugated fatty acid methyl ester. In these embodiments, the present invention provides methods comprising alcoholysis of the lactone ring of the allylic lactones under acidic catalysis (MeOH/H$^+$), which result in methyl esters of the tetraenoic conjugated acids described above as the main products of the reaction. Typically, the allylic lactone is provided in a solvent (in particular methanol), and a concentrated acid (in particular, sulfuric acid) in a solvent (in particular, the same solvent and/or methanol) is added. The reaction mixture is sealed in an ampule and incubated at elevated temperatures (in particular, about 80° C.) for a sufficient time (in particular, about 1 hour) to produce polyconjugated fatty acid methyl esters. In further embodiments, after cooling, the methyl ester products are extracted; in yet further embodiments, the products are dried, filtered, and stored at low temperature (in particular, at about −80° C.). In further embodiments, different isomeric forms of particular conjugated fatty acid methyl esters are further purified, for example by HPLC. Exemplary methods are provided in Example 2. Exemplary products include the methyl esters of 4E,6E,8E,10Z,13Z,16Z,19Z-docosaheptaenoic acid and 4E,6E,8E,10E,13Z, 16Z, 19Z-eicosahexaenoic acid prepared from gamma-lactone 4-HDHE, 5E,7E,9E,11Z,14Z,17Z-eicosahexaenoic and 5E,7E,9E,11E,14Z,17Z-eicosahexaenoic prepared from δ-lactone of 5-HEPE, and from the δ-lactone of 5-HETE 5E,7E,9E,11Z,14Z-eicosapentaenoic and 5E,7E,9E,11E,14Z-eicosapentaenoic acid.

The conjugated fatty acids methyl esters are identical to those synthesized by first the action of DBU on iodolactone and then esterification of the resulting products by diazomethane. In these embodiments as well, the lactone ring size is not limiting.

Alternatively, iodolactones can be used to produce polyconjugated fatty acid methyl esters in a series of reactions, in which the last reaction involves DBU. In these embodiments, the present invention provides methods comprising transformation of a natural system of methylene interrupted double bonds by reacting isomeric mixtures of vicinal bromoacetates with DBU. Thus, bromoacetates are synthesized from corresponding epoxides obtained from iodolactones. The reaction between these bromoacetates and DBU leads to formation of polyconjugated fatty acid methyl esters with the identical tetraenoic conjugated fragments as are observed in the methyl esters obtained by acidic alcoholysis of allylic lactones (described above) and in those obtained directly from iodolactones (described below).

In these embodiments, the present invention provides methods for synthesizing a methyl ester of an epoxy fatty acid from an iodolactone substrate as described above. The methods comprise providing an iodolactone of a polyunsaturated fatty acid in a solvent (in particular, methanol) and adding triethylamine. The reaction mixture is refluxed for a period of time sufficient to produce a methyl ester of an epoxy fatty acid product (in particular, about 3 hours), then evaporated under a vacuum. In further embodiments, the residue is dissolved in a solvent (in particular, hexane); in yet further embodiments, the dissolved residue is filtered, evaporated under vacuum, and purified (as for example, by column chromatography; in particular where the column is silica gel, and the methyl ester of an epoxy fatty acid product is eluted with, for example, a gradient of ether in hexane). Exemplary methods are provided in Example 2. Exemplary products are shown in FIG. 1.

In other of these embodiments, the present invention provides methods for synthesizing a bromoacetate from an methyl ester of an epoxy fatty acid. Typically, the methods comprise providing a methyl ester of an epoxy fatty acid in a solvent (in particular, in dry ether) and adding acetylbromide (typically in the same solvent; in particular, in dry ether). The reaction mixture is incubated at about room temperature for a period of time sufficient to produce a bromoacetate product (typically, about one hour). In further embodiments, the reaction mixture is washed with an aqueous solution (in particular, with water and with a salt solution, where in particular embodiments the solution is a saturated salt solution, and in other embodiments the salt is NaCl). In yet further embodiments, the washed reaction mixture is dried (in particular embodiments, over $Na_2SO_4$). In yet further embodiments, the dry extract is filtered, evaporated under a vacuum, and purified, as for example by column chromatography (in particular embodiments, the column is a silica gel, and the product is purified with a gradient of ether in hexane). Exemplary methods are provided in Example 2. Exemplary products are shown in FIG. 1.

In yet other of these embodiments, the present invention provides methods for formation of tetraenoic conjugated fatty acids by reaction of the bromoacetates with DBU. In some embodiments, the methods comprise providing a solution of the bromoacetates (for example, as described above) (in particular embodiments, the solvent is dry benzene) and adding DBU (in particular embodiments, the DBU is dry; in other particular embodiments, the DBU is added at about 1.5 equivalents). The reaction mixture is incubated at about room temperature for a sufficient time to produce polyconjugated fatty acid methyl esters. In yet further embodiments, the reaction mixture is further treated as described above for the synthesis of conjugated fatty acids from iodolactones (reaction (1) of FIG. 1), and further stored in solution (in particular embodiments, the solvent is methanol) at low temperature (in particular embodiments, the temperature is about −60° C.).

However, unexpectedly, it is possible to prepare a polyconjugated fatty acid directly from a corresponding iodolactone in a single, novel reaction. In these embodiments, the present invention provides a modification of the reaction of an iodolactone of HUFA with DBU described above, where the modification is to use a molar excess of DBU to iodolactones of HUFAs. In particular embodiments, DBU is present in a molar excess about 2 to 2.5 fold over the iodolactones. Thus, in these embodiments, an iodolactone of a HUFA is reacted with about a 2 to about a 2.5 molar excess of DBU; products of this reaction comprise fatty acids with four conjugated double bonds as major products, instead of the initially expected fatty acids with trienoic conjugation. These initially expected products were based upon a reaction of double eliminations according to E2 mechanism. Although it is not necessary to understand the mechanism in order to practice the invention, and the invention is not intended to be limited to any particular mechanism, it was initially believed that it would be possible to eliminate H-J (from position 7 and 6 in AA and EPA or from position 6 and 5 in DHA) and H—OOC— (from position 4 and 5 in AA and EPA or from position 3 and 4 in DHA) to result in the corresponding position of the conjugated double bonds at delta 5,7,9—in AA and EPA or at delta 3,5,7—in DHA. Instead, an elimination together with a shift of double bonds to form delta 5,7,9,11—conjugated system (AA and EPA) and delta 4,6,8,10—(DHA) was observed, where the shift was unexpected.

Typically, an iodolactone of a HUFA is dissolved in a solvent to which is added DBU; the reaction mixture is incubated in the dark under an inert atmosphere for a sufficient time to form a polyconjugated fatty acid. In particular embodiments, dry benzene is used as the solvent (in even more particular embodiments, the benzene is distilled over $P_2O_5$); and in other particular embodiments, dry DBU reagent is used (in even more particular embodiments, DBU is distilled over $CaH_2$ at reduced pressure); and in other particular embodiments, both dry benzene and dry DBU are used. Under some reaction conditions, using non-dry benzene and non-dry DBU (i.e., without the treatments described above) leads only to formation of by-products. Exemplary but non-limiting methods and reaction conditions are provided in Examples 2 and 3. Exemplary products include polyconjugated fatty acids 5E,7E,9E,11Z,14Z,17Z-eicosahexaenoic acid and 5E,7E,9E,11E,14Z,17Z-eicosahexaenoic acid from δ-iodolactone of EPA, 4E,6E,8E,10Z,13Z,16Z,19Z-docosaheptaenoic acid and 4E,6E,8E,10E,13Z,16Z, 19Z-docosaheptaenoic acid form γ-iodolactone of DHA, and 5E,7E,9E,11Z,14Z-eicosapentaenoic acid and 5E,7E,9E,11E,14Z-eicosapentaenoic acid from δ-iodolactone of AA.

In further embodiments of the invention, 4-methyl-1,2,4-triazoline-3,5-dione (MTAD) adducts from conjugated fatty acids for mass spectrometric analysis are synthesized; in particular embodiments, the synthesis is essentially as described by Dobson (Dobson, G. (1998) J. Am. Oil Chem. Soc. 75:137–142). Exemplary methods are provided in Example 2. In yet further embodiments of the present invention, oxazolines of conjugated fatty acids are synthesized for mass spectrometric analysis; in particular embodiments, the synthesis is essentially the same as that reported recently (Kuklev, D. V., and W. L. Smith (2003) J. Lipid. Res. 44:1060–1066). Exemplary methods are provided in Example 2.

Analysis of the reaction products by HPLC demonstrated: the absence any remarkable amounts of conjugated triene-containing species (i.e., materials with absorption maxima at 270–280 nm); the identity of products obtained from the given fatty acids using different techniques as determined by their spectral properties and chromatographic mobilities; that the systems of double bonds consist only of carbon-carbon double bonds possessing well-defined UV spectral features and insensitivity to reduction by $LiAlH_4$. The reaction mixture major products were very similar to one another; therefore, the detailed description of the compounds derived from natural eicosapentaenoic acid (as described in Example 3) are exemplary of the other products obtained.

In other embodiments, the present invention provides methods of purification and isolation of the conjugated polyunsaturated fatty acid products. Purification of the conjugated polyunsaturated fatty acids presented problems because these acids readily undergo isomerisation, polymerization, and oxidation (Johnson, R. W., and E. H. Pryde (1979) In Fatty Acids (E. H. Pryde, editor; American Chemical Society, Champaign, Ill.) 319–342; Frankel, E. N. (1979) In Fatty Acids (E. H. Pryde, editor; American Chemical Society, Champaign, Ill.) 426–456; and Johnson, R. W (1979). In Fatty Acids (E. H. Pryde, editor; American Chemical Society, Champaign, Ill.) 342–352; and Lopez, A., and W. H. Gerwick. (1987) Lipids 22:190–194). Thus, for example, the use of hexane or ether for extraction led to isomerisation, whereas evaporation of solvents under vacuum or in stream of inert gas lead to partial polymerization. Moreover, the use of $CuSO_4 \times 7H_2O$ or $AgNO_3$ is a very common technique for halogen trapping, and $CuSO_4 \times 7H_2O$ is used for DBU trapping. However, these techniques as well cannot be used with polyconjugated fatty acid products, as their use leads to polymerization of the polyconjugated fatty acid products.

Thus, because these fatty acids are readily polymerized, it is not possible to utilize commonly used techniques for purifying and isolating the polyconjugated fatty acid products. Thus, in some embodiments, the methods comprise clarifying the polyconjugated fatty acid solution by removing a precipitate from the solution; in different embodiments, the precipitate is removed by centrifugation or by filtration. The precipitates can be subsequently washed, and the wash combined with the initial clarified solution. In further embodiments, the solvent of the clarified solution is evaporated; in particular embodiments, diglyme (preferably dry) is added before evaporation. Diglyme is a high boiling solvent, and a solvent that can be eliminated by solid phase extraction on a reversed phase cartridge from the polyconjugated fatty acid products. Thus, diglyme is used to prevent polymerization of the conjugated fatty acid products while evaporating them to dryness. Other high boiling solvents, such as triglyme or tetraglyme or DMSO, can also be used. In other particular embodiments, evaporation is under a vacuum or under an inert atmosphere (such as nitrogen); in other particular embodiments, evaporation is at about 30° C. or less. In further embodiments, the evaporated residue is dissolved in a water/alcohol/acid solution; in particular embodiments, the alcohol is methanol, and the acid is acetic acid. In yet further embodiments, the polyconjugated fatty acid product is isolated by chromatography, as for example on a solid phase extraction cartridge which is eluted with water and then with alcohol, such as methanol, in which the polyconjugated fatty acid elutes. In yet further embodiments, the solution comprising the polyconjugated fatty acid is diluted (in particular with water) and the polyconjugated fatty acid concentrated, for example with a guard column. In yet further embodiments, the concentrated polyconjugated fatty acid is crystallized for a sufficient period of time at very low temperatures; in particular embodiments, the fatty acid is crystallized over night at about −80° C. Particular embodiments of purification and isolation are provided in Example 2. With these methods, it is possible to transfer these fatty acid products not only to methanol but to also methylene chloride and to chloroform (or CDCl$_3$), for subsequent analysis by $^1$H-NMR.

In other embodiments, the present invention provides novel methods for the synthesis of parinaric acid isomers. In some embodiments, the parinaric acid isomers are synthesized from alpha-linoleic acids (ALA). In some embodiments, the ALA is prepared from flax oil. For example, in some embodiments, flax oil is first enriched for free fatty acids (e.g., using the methods described in the illustrative examples below). In some embodiments, the free fatty acids are enriched for ALA by crystallization (See, e.g., the illustrative examples below). In some embodiments, the ALA enriched fatty solution is then brominated using a bromine solution to generate ALA bromides. In certain embodiments, the ALA bromides are dehydrobrominated using DBU. The resulting extract is then purified to generate parinaric acid isomers. In certain embodiments, the parinaric acid isomers are separated (e.g., using HPLC). The methods of the present invention (See e.g., Example 4 and FIGS. 8 and 9) resulted in the generation of α-parinaric acid and two of its isomers as well as β-parinaric acid.

Utility of Novel Polyconjugated Fatty Acids

The novel polyconjugated fatty acids of the present invention have a number of utilities. In some utilities, they are used as research tools. Research tools include their use as a probe, due to their similarity to essential fatty acids and to their fluorescent nature. The novel fatty acids of the present invention have pronounced spectral properties that are quite different from those of natural fatty acids, and that allows identification of them in fatty acids mixtures, and in model and biological membranes. In these uses, the polyconjugated fatty acid products can taken up by cells, and their movement monitored, preferably spectrally. In other utilities, the biological effects of these fatty acids are investigated; these fatty acids are contemplated to have unusual biological effects, due to their similarity to essential fatty acids. Moreover, because of the sensitivity of the tetraene group to light, polyconjugated fatty acid products of the present invention have the potential for being used in tracking fatty acid movements in cells employing fluorescence techniques and in UV light-induced cross linking to membrane proteins.

The unique spectral properties, which are described in more detail in the Examples, can be summarized as follows. Polyconjugated fatty acid products of the present invention have quite unusual UV properties of absorption at 300 nm with molar extinction coefficient at about 74000. These UV properties allows the presence of these polyconjugated fatty acid products in a mixture of common fatty acids to be monitored by the use of common laboratory UV spectrophotometers. Moreover, polyconjugated fatty acid products of the present invention exhibit fluorescence, which property is quite unusual for natural fatty acids or their mixtures. Thus, the fluorescent property allows the presence of these polyconjugated fatty acid products in a mixture of common fatty acids to be monitored by applying UV irradiation at 300 nm and collecting the signal at 420 nm. In addition, polyconjugated fatty acid products of the present invention have unusual chromatographic mobility, as they do not overlap with the parent fatty acids while RP-HPLC analysis, and so can be identified easily.

Thus, for example, initial experiments have examined cellular uptake and metabolism of 5E,7E,9E,11E,14Z,17Z-eicosahexaenoic acid in HEK293 cells. 5E,7E,9E,11E, 14Z, 17Z-eicosahexaenoic acid was taken up by the cells and assimilated into complex lipids, as determined by fractionation of organic extracts on aminopropyl columns. However, unlike AA or EPA, 5E,7E,9E,11E,14Z,17Z-eicosahexaenoic acid appeared not to be elongated efficiently to a 22 carbon fatty acid, suggesting that the conjugated fatty acids are poor substrates for elongases. 5E,7E,9E,11E,14Z,17Z-eicosahexaenoic acid appears to be oxidized through a monooxygenation system in HEK293 cells, and the products released to the medium.

In other utilities, the present invention contemplates the use of fatty acid products of the present invention in animal feeding studies and as nutritional supplements, as well as for therapeutic treatments. It is contemplated that the purified polyconjugated fatty acid products of the present invention can be used as controls in animal feeding studies so that the biological effects (e.g., partitioning within organs and cells, effects on lipid biosynthesis, and metabolism) of the fatty acid products can be studied. The polyconjugated fatty acid products may be provided as free fatty acids, alkylesters (for example, as methyl or ethyl esters of polyconjugated fatty acids), triglycerides, or combinations thereof. In some preferred embodiments, the polyconjugated fatty acid products are provided orally. In other embodiments, the polyconjugated fatty acid products may be formulated with suitable carriers such as starch, sucrose or lactose in tablets, pills, dragees, capsules, solutions, liquids, slurries, suspensions and emulsions. Preferably, the polyconjugated fatty acid products formulations contain antioxidants, including, but not limited to BHT, lecithin, and oil soluble forms of vitamin C. The polyconjugated fatty acid products may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the polyconjugated fatty acid products are provided as soft gelatin capsules. The polyconjugated fatty acid products may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

An effective amount of polyconjugated fatty acid products may also be provided as a supplement in various food products, including animal feeds. For the purposes of this application, "food products containing polyconjugated fatty acid products" refers to any natural, processed, diet or non-diet food product to which exogenous polyconjugated fatty acid products have been added. Likewise, "feed products" refer to animal feed to which exogenous polyconjugated fatty acid products have been added. The polyconjugated fatty acid products may be added in the form of free fatty acids, methyl esters, or as an oil containing partial or whole triglycerides of polyconjugated fatty acids. Therefore, polyconjugated fatty acid products may be directly incorporated into various food products.

In some embodiments of the present invention, the polyconjugated fatty acid products are used as a mixture of polyconjugated fatty acid products synthesized from a mixture of starting HUFAs. In other embodiments, the polyconjugated fatty acid products are further purified by separation into separate polyconjugated fatty acid products, for example as described above.

In still further embodiments, the present invention provides methods for the synthesis of parinaric acid isomers (See above). Such isomers find use in a variety of applications. For example, in some embodiments, parinaric acid is used as a fluorescent membrane probe (Sklar et al., Proc Natl Acad Sci USA 1975, 72, 1649–1653) ands the detection of phase transitions in bilayers (Sklar et al., Biochemistry 1977, 16, 819–828; Sklar et al., Biochemistry 1977, 16, 813–819; Sklar et al., Biochemistry 1977, 16, 5100–8; Sklar et al., Biochemistry 1979, 18, 1707–16). Parinaric acids are also widely used as probes for investigating membrane structure including lipid-protein interaction (Narayanaswami et al., Biochemistry 1993, 32, 12420–7), lipid clustering (Brewer and Matinyan, Biochemistry 1992, 31, 1816–20), lipid transport processes including structural characterization of lipoproteins (Ben-Yashar and Barenholz, Chem Phys Lipids 1991, 60, 1–14), fatty acid-binding proteins (Hubbel and Altenbach, C. (1994) In *Membrane protein structure: experimental approaches*(Ed, White, S. H.) Oxford University Press, New York, pp. 224–248) and phospholipid transfer proteins (Kasurinen et al., Biochemistry 1990, 29, 8548–54). In the field of lipid peroxidation, parinaric acids are used for evaluating antioxidants (Suzuki et al., Biochemistry 1993, 32, 10692–9.), measuring peroxidation in lipoproteins (Tribble et al., PNAS 1994, 91, 1183–1187) and for investigating relationships between peroxidation and cytotoxicity (Crook et al., Cell 1994, 79, 817–27) and apoptosis (Hockenbery et al., Cell 1993, 75, 241–51).

Experimental

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); μm (nanometers); ° C. (degrees Centigrade); AA (arachidonic acid); EPA (eicosapentaenoic acid); DHA (docosahexaenoic acid); $Q^a$ (fluorescent yield); DBU (1,8-diazobicyclo[5.4.0]undec-7-ene); MTAD (4-methyl-1,2,4-triazoline-3,5-dione); 4-HDHE (4-hydroxy,5E,7Z,10Z,13Z,16Z,19Z-docosahexaenoic acid); TMS (trimethylsilyl); 5-HEPE (5-hydroxy,6E,8Z,11Z,14Z,17Z-eicosapentaenoic acid); 5-HETE (5-hydroxy,6E,8Z,11Z,14Z-eicosatetraenoic acid); THR (tetrahydrofuran); HUFA (highly unsaturated fatty acid); PUFA (polyunsaturated fatty acid).

EXAMPLE 1

This example describes reagents and equipment used in synthesis and analysis of polyconjugated fatty acids.

Reagents. Arachidonic acid (AA; 90%) and 1,8-diazobicyclo[5.4.0]undec-7-ene (DBU) were purchased from Sigma Chemical Co. (St. Louis, Mo.). Fish oil (28% eicosapentaenoic acid (EPA) and 23% docosahexaenoic acid (DHA)) was purchased from Walmart. Trifluoroacetic anhydride, ethanolamine, isobutylchloroformate, pyridine, pyrrolidine and 4-methyl-1,2,4-triazoline-3,5-dione were products of Aldrich Chemical Co. (Milwaukee, Wis.) with purities ≧96%. Benzene, hexane, ether and acetonitrile were distilled over phosphorus pentoxide and triethylamine, tetrahydrofuran (THF) and methanol were distilled over metallic sodium before use. DBU was distilled over $CaH_2$ in vacuo. Silica gel "Selecto" 32–63 μm was purchased from Selecto Scientific (Georgia, USA). Thin layer chromatography (TLC) plates were purchased from Sigma Chemical Co. Compounds on TLC plates were visualized by spraying the plates with a 5% solution of phosphomolybdic acid in methanol and then heating the plates for 2–3 min at about 100° C.

Equipment. Mass spectra were obtained using a Hewlett-Packard 5890 gas chromatograph coupled to a Hewlett-Packard 5970 series mass selective detector operated with a Hewlett-Packard 7946 computer. Gas chromatography conditions were as follows: He was used as the carrier gas at a flow rate of 35 cm/sec; the oven temperature was kept at 210° C.; the injector temperature was 250° C.; the interface temperature was 250° C.; separations were on a capillary column DB-5 ms (30 m×0.32 mm, 1 mkm; J&W, USA); the injector split ratio was kept constant at 1:60. The mass detector conditions were as follows: the electron energy was 70 eV; the emission current was 0.8 mA; the accelerating voltage was 8 kV; the scale was from 50 to 1000.

HPLC analysis and preparative separations were performed on an Alliance HPLC system (Waters, USA) equipped with a Waters 2695 separation module and a Waters 2996 photodiode array detector. Analytical RP-HPLC was performed on a Nucleosil-C18 analytical column (4.6×250 mm, 5 μm; Xpertek", USA). Solid phase extraction was performed on Luna-2 C18 guard column (10×50 mm, 10 μm; Phenomenex, Calif., USA). Preparative separations were performed on a Kromasil C18 column (10×250, 5 μm; Xpertek, USA). $^1$H-NMR spectra were recorded on an INOVA-300 spectrometer (Varian, USA) operated at 300 MHz; for samples dissolved in $CDCl_3$, tetramethylsilane was used as the internal standard. All of the signal assignments were performed on the basis of selective decoupling experiments. All of the UV-VIS spectra were recorded on a Hewlett-Packard 8453 instrument; the UV-VIS spectrophotometer was operated with ChemStation data processing software.

EXAMPLE 2

This example describes methods used in synthesis and analysis of polyconjugated fatty acids.

Preparation of Iodolactones of DHA, EPA and AA.

A mixture of fish oil fatty acids (43.5 g, 28% EPA and 23% DHA) was dissolved in 150 ml of ethanol and 230 ml of a 7.5% solution of $KHCO_3$ (17.3g of $KHCO_3$; 1.2 eq per total fatty acid) was added to give a clear solution of fatty acid salts. A solution of 27 g of $I_2$ in 300 ml of ethanol (1.5 eq per EPA plus DHA) and 500 ml of hexane were added to the clear solution with vigorous stirring. The reaction mixture was kept at room temperature (24° C.) for 16 hr, the hexane layer was removed and the reaction mixture was extracted with hexane (3×500 ml). The combined hexane layers were washed sequentially with aqueous 5% $Na_2S_2O_3$ (250 ml), water (500 ml) and saturated aqueous NaCl (200 ml) and then dried over anhydrous $Na_2SO_4$ and evaporated under vacuum. The crude oily product (24.9 g, indicating ≧75% yield) was dissolved in dry benzene (30 ml) and after addition of 2 g of BHT was stored at −80° C. Aliquots of this crude mixture of the γ-iodolactone of DHA (Ic, FIG. 1) and the δ-iodolactone of EPA (Ib, FIG. 1) were purified by column chromatography on silica gel as required to isolate the individual iodolactones. The purification is preferably performed quickly using a 25-33-fold weight excess of silica gel as the adsorbent and elution with a gradient of ether in benzene (0–5%). To prevent on column degradation of the iodolactones, the column is prewashed with 1% BHT in dry benzene.

In the case of arachidonic acid its δ-iodolactone (Ia, FIG. 1) was synthesized from a commercially available concentrate with an AA content of about 90%. The yield of chromatographically pure product was 62%. The spectral properties of compounds Ia–c (FIG. 1) were in excellent agreement with those reported earlier (Corey, E. J. et al. (1983) Proc Natl Acad Sci USA 80(12):3581–3584; Wright, S. W. et al. (1987) J. Org. Chem. 52(19):4399–4301; and Kuklev, D. V. et al. (1991) Bioorganicheskaya Khimiya 17(11):1574–1581).

Reaction of iodolactones with excess DBU to form polyconjugated fatty acids (FIG. 1, reaction (1)). The δ-iodolactone of eicosapentaenoic acid (Ib; FIG. 1) (1.30 g, 3.0 mmol) was dissolved in 15 ml of dry benzene and a solution of 1.2 g (7.9 mmol) of dry DBU in 15 ml of dry benzene was added. The reaction mixture was left at room temperature under nitrogen for 72 hr in the dark. The yield of the expected conjugated fatty acids (IIIb, FIG. 1) determined spectrophotometrically was 93% ($\epsilon(303\ nm)=74{,}000\ 1\ mol^{-1}\ cm^{-1}$). Spectral information is presented below in Example 3.

Similarly, from 1.4 g (3.1 mmol) of the γ-iodolactone of docosahexaenoic acid (Ic, FIG. 1) through the action of 1.2 g (7.9 mmol) of dry DBU, the conjugated fatty acids (IIIc) were obtained with a yield of 95%. The composition of the mixture of tetraenoic fatty acids was about 90% 4E,6E,8E,10Z,13Z,16Z,19Z-docosaheptaenoic acid and about 10% 4E,6E,8E,10E,13Z,16Z,19Z-docosaheptaenoic acid as determined by HPLC.

4E,6E,8E,10Z,13Z,16Z,19Z-Docosaheptaenoic acid exhibited the following spectral properties: UV (methanol): $\lambda_{max}=290, 303, 317$ nm; $\epsilon$ (303 nm)=74,000 1 $mol^{-1}$ $cm^{-1}$. Fluorescence (methanol): Em $\lambda_{max}=428$ nm; $Q^a=0.017$. MS of oxazoline (m/z, (I%)): $[M]^+351$ (17), $[M-1]^+350$ (10), $[M-CH_3]+336$ (5), $[M-C_2H_5]^+322$ (7), 202 (12), 242 (12), 282 (18), 322 (5), 85 (100), 98 (55), 111(30) (Δ4 double bond) and 141 (33). RP-HPLC ($C_{18}$ column eluted with 85:15:0.1, methanol-$H_2O$-acetic acid): k'=8.8. $^1H$-NMR: δ 0.95 (3H, t, J=7.5 Hz, H-22), 2.06 (2H, m, $H_2$-21), 2.35 (2H, m, $H_2$-3), 2.4 (2H, m, $H_2$-2), 2.80 (4H, m, $H_2$-15,18), 2.88 (2H, m, $H_2$-12), 5.36 (7H, m, H-11,13,14,16,17,19,20), 5.66 (1 H, dt, $J_{5,6}=14.4$ Hz, $J_{54}=6.9$ Hz, H-4), 6.08 (1H, m, H-10), 6.18 (4H, m, H-5,6,7,8), 6.46 (1H, dd, $J_{9,8}=13.5$, $J_{9,10}=11.1$, H-9).

4E,6E,8E, 10E,13Z,16Z,19Z-Docosaheptaenoic acid yielded the following spectral data: UV (methanol): $\lambda_{max}=289, 300, 315$ nm; $\epsilon$ (300 nm)~80,000 1 $mol^{-1}$ $cm^{-1}$. Fluorescence: Em $\lambda_{max}=422$ nm; $Q^a=0.013$. RP-HPLC ($C_{18}$ column eluted with 85:15:0.1, methanol-$H_2O$-acetic acid) k'=9.5. MS of oxazoline the same as for its isomer noted above; MS of the MTAD adduct (m/z (I%): $[M]^+$ 453 (3), $[M-C_4H_7O_2]^+$ 366(11), $[M-C_4H_7O_2-C_2H_3NO]^+$ 309 (6), $[M-C_{11}H_{17}]^+$ 304(8). $^1H$-NMR: δ 0.95 (3H, t, J=7.5 Hz, H-22), 2.06 (2H, m, $H_2$-21), 2.35 (2H, m, $H_2$-3), 2.4 (2H, m, $H_2$-2), 2.80 (4H, m, $H_2$-15,18), 2.88 (2H, m, $H_2$-12), 5.36 (6H, m, H-13,14,16,17,19,20), 5.66 (2H, m, $J_{4,5}\approx J_{10,11}=14.5$, $J_{11,12}=7$, H-4,11), 6.13 (6H, m, H-5,6,7,8,9,10).

Similarly, from 1.58 g (3.7 mmol) of the δ-iodolactone of arachidonic acid (Ia, FIG. 1) and the action of 1.4 g (9.2 mmol) of dry DBU, the conjugated fatty acids (IIIa, FIG. 1) were obtained in a yield of 95% (determined spectrophotometrically). The composition of the mixture of tetraenoic fatty acids determined by HPLC was 85% 5E,7E,9E,11Z,14Z-eicosapentaenoic acid and 15% 5E,7E,9E,11E,14Z-eicosapentaenoic acid.

5E,7E,9E,11Z,14Z-Eicosapentaenoic acid exhibited the following spectral properties: UV (methanol): $\lambda_{max}=290, 303, 317$ nm; $\epsilon$ (303 nm)=74,000 1 $mol^{-1}$ $cm^{-1}$. RP-HPLC ($C_{18}$ column eluted with 85:15:0.1, MeOH—$H_2O$-acetic acid) k'=9.7. Fluorescence (methanol): Em $\lambda_{max}=428$ nm; $Q^a=0.015$. MS of oxazoline (m/z, (I%)): $[M]^+327$ (41), $[M-1]+326$ (35), $[M-Me]^+$ 312 (15), $[M-C_5H_{11}]^+$ 256 (11), $[M-C_7H_{13}]^+$ 230 (7), $[M-C_8H_{11}]^+$ 216 (10), 98 (35), 85 (100). $^1H$-NMR (300 MHz, $CDCl_3$, δ, ppm): 0.89 (3H, t, J=7 Hz, $H_3$-20), 1.33 (6H, m, $H_2$-17,18,19), 1.73 (2H, tt, $J_{32}=7.5$; $J_{34}=7.4$, H-3), 2.03 (2H, m, $H_2$-16), 2.23 (2H, bdt, $J_{43}=7.4$, $J_{45}=6.9$, $H_2$-4), 2.33 (2H, t, $J_{23}=7.5$, $H_2$-2), 2.95 (2H, m, H-13), 5.36 (3H, m, H-12,14,15), 5.64 (1H, dt, $J_{5,6}=14.4$ Hz, $J_{54}=6.9$ Hz, H-5), 6.09 (1H, m, H-6), 6.18 (4H, m, H-7,8,9,11), 6.47 (1H, dd, $J_{10,9}=13.7$, $J_{10,11}=11$, H-10).

5E,7E,9E,11E,14Z-eicosapentaenoic acid exhibited the following spectral properties: UV (methanol): $\lambda_{max}=289, 300, 315$ nm; $\epsilon$ (300 nm)~80000 1 $mol^1$ $cm^{-1}$. RP-HPLC ($C_{18}$ column eluted with 85:15:0.1, MeOH—$H_2O$-acetic acid) k'=10.6. Fluorescence (methanol): Em $\lambda_{max}=428$ nm; $Q^a=0.013$. MS of oxazoline is the same as that noted above for its isomer. Mass spectrometry of methyl ester of MTAD adduct (m/z (I%)): $[M]^+$ 429 (8), $[M\ -C_8H_{15}]^+$ 318 (50). $^1H$-NMR: 0.89 (3H, t, J=7 Hz, $H_3$-20), 1.33 (6H, m, $H_2$-17,18,19), 1.73 (2H, tt, $J_{32}=7.5$; $J_{34}=7.4$, H-3), 2.03 (2H, m, $H_2$-16), 2.23 (2H, bdt, $J_{43}=7.4$, $J_{45}=6.9$, $H_2$-4), 2.33 (2H, t, $J_{23}=7.5$, $H_2$-2), 2.95 (2H, m, $H_2$-13), 5.39 (2H, m, H -14,15), 5.68 (2H, m, $J_{5,6}\approx J_{11,12}=14.5$, $J_{5,4}\approx J_{12,13}=7$, H-5,12), 6.13 (6H, m, H-6,7,8,9,10,11).

Conjugated fatty acids were purified as follows. The reaction mixture was transferred to a centrifuge tube and centrifuged at 1000×g for 5 min. The clear solution was separated from the precipitate which was then stirred vigorously with dry benzene (25 ml) and centrifuged again, and the clear benzene solutions were combined. The solution was transferred to an evaporating flask, 5 ml of dry diglyme (2-methoxyethyl ether) was added, and the mixture was evaporated under vacuum keeping the bath temperature at less than 30° C. To the resulting solution of the reaction mixture in diglyme were added 5 ml of methanol, 5 ml of water and 600 μl of acetic acid. The mixture was stirred for 30 sec and put on a solid phase extraction cartridge (prewashed with 10 ml of methanol and then 10 ml of water). The cartridge was eluted with 15 ml of water, 30 ml of a methanol-water mixture (50:50, v/v) and 2 ml of methanol. All the fatty acid was found in the methanol fraction. To the solution of the conjugated fatty acid was added 6 ml of water, and the resulting solution was pumped through a "guard" column (50×10 mm, C18, 10 μm, equipped with PEEK frits (Waters)). After concentrating the fatty acid, the guard column was attached to a preparative HPLC column (C18, 250×10 mm, 5 µm, equipped with PEEK frits), and the system was washed with methanol-water-acetic acid (85:15: 0.1). The fractions containing the purified fatty acid product were combined and placed −80° C. After an overnight crystallization, a white precipitate of the conjugated fatty acid was collected.

Reaction of the iodolactones with equimolar DBU to form allylic lactones (FIG. 1, reaction (2)). The γ-iodolactone of docosahexaenoic acid (Ic, FIG. 1) (2.10 g; 4.63 mmol) was dissolved in 15 ml of dry benzene and a solution of dry DBU (770 µl; 5.1 mmol) in 15 ml of dry benzene was added. The reaction mixture was stirred at room temperature under nitrogen for 12 hr in the dark, then transferred to a centrifuge tube and centrifuged at 1000×g for 5 min. The clear solution was separated from the precipitate which was then vigorously stirred with dry benzene (25 ml) and centrifuged again, and the clear benzene solutions were combined. The resulting solution was evaporated under vacuum, the dry residue dissolved in a small amount of benzene and after addition of 0.25 g of BHT, the sample was purified by column chromatography on 60 g of silica gel using a gradient of dry ether in dry benzene (0–7%). The yield was 1.03 g (68%) of the γ-lactone of 4-HDHE (4-hydroxy,5E, 7Z,10Z,13Z,16Z,19Z-docosahexaenoic acid) (IIc, FIG. 1)) as a pale yellow oil.

Similarly, from δ-iodolactones of EPA (Ib, FIG. 1) and AA (Ia, FIG. 1), the corresponding δ-lactones of 5-HEPE (5-hydroxy,6E,8Z,11Z,14Z,17Z-eicosapentaenoic acid) (IIb, FIG. 1) and 5-HETE (5-hydroxy,6E,8Z,11Z,14Z-eicosatetraenoic acid) (IIa, FIG. 1) were synthesized in yields, of 72% and 71%, respectively. The spectral properties of these newly synthesized compounds are in agreement with those reported previously (Corey, E. J. et al. (1983) Proc Natl Acad Sci USA 80(12):3581–3584; Wright, S. W. et al. (1987) J. Org. Chem. 52(19):4399–4301; Corey, E. J. et al. (1980) Am. Chem. Soc. 102(4):1435–1436; and Kuklev, D. V., and V. V. Bezuglov (1998) In Modified Fatty Acids (D. V. Kuklev, editor; Dalpribor PbsH, Vladivostok, Russia) pp 1–16).

Reaction of the allylic lactones with excess of DBU to form the polyconjugated fatty acids (FIG. 1, reaction (10)). The reaction conditions for the reaction of the allylic lactones with excess of DBU to form the polyconjugated fatty acids is the same as that described above for the reaction between the iodolactones and DBU. Thus, about 2.6 mol of DBU was added to about 1 mol of iodolactones. This is the same relative amount of DBU used for the reaction with allylic lactones (about 2.6 mol of DBU to about 1 mol of an allylic lactone). Thus, from of γ-lactone of 4-HDHE (Ic, FIG. 1) the corresponding polyconjugated fatty acids were obtained in yield of 93% (determined spectrophotometrically). Similarly, from δ-lactones of EPA (IIb, FIG. 1) and AA (IIa, FIG. 1) the corresponding polyconjugated fatty acids were obtained in yields of 86%.

Base cleavage of allylic lactone ring—hydroxy acid formation (FIG. 1, reaction (6)). To a solution of 236 mg (0.72 mmol) of the γ-lactone of 4-HDHE in 5 ml of ethanol were added 1 ml of 1.5 N KOH, 3 ml of ethanol and 3 ml of water, and the reaction mixture was stirred for 16 hr at room temperature. Water (10 ml) was added, and the solution was acidified to pH 4 with 1.5 N HCl and extracted with hexane-ether (1:1) (3×10 ml). The resulting organic extract was washed with water (2×20 ml) and then a saturated solution of NaCl and dried over $Na_2SO_4$. The dry extract was filtered and evaporated under vacuum to yield 214 mg (86%) of 4-HDHE. Similarly, 5-HETE and 5-HEPE were synthesized from their corresponding γ-lactones in yields of more than 85%. The spectral properties of these hydroxy fatty acids were identical to those reported previously (Solodovnik, V. D. (1967) Russian Chemical Reviews 36:272–283; Corey, E. J. et al. (1980) J. Am. Chem. Soc. 102(4):1435–1436; and Kuklev, D. V., and V. V. Bezuglov (1998) In Modified Fatty Acids (D. V. Kuklev, editor; Dalpribor PbsH, Vladivostok, Russia) pp 1–16).

Synthesis of methyl esters of TMS-ethers of the hydroxy acids. (FIG. 1, reaction (7)). 4-HDHE (60 mg) was converted to its methyl ester using freshly distilled diazomethane in ether. The solvent was evaporated and the sample dissolved in 1 ml of dry pyridine (freshly distilled over $CaH_2$). Chlorotrimethylsilane (50 ml) was added, and the reaction mixture kept at 70° C. for 2 hr. After cooling, the reaction mixture was evaporated under a stream of nitrogen and the dry residue was dissolved in 2–5 ml of hexane and filtered through 500 mg of silica gel. The trimethylsilylether of the methyl ester of 4-HDHE had an $R_f$ approximately 0.9 (hexane-ether, 1:1) and was used without further purification. Similar procedures were used to obtain the methyl esters of 5-HETE and 5-HEPE and their corresponding trimethylsilylethers.

Cleavage of the TMS-ether of allylic alcohols under acidic conditions. Formation of tetraenoic polyconjugated and polyunsaturated fatty acid methyl esters (FIG. 1, reaction (8)). The dry oil of the trimethylsilylether of the methyl ester of 5-HEPE (about 50 mg) (IVb, FIG. 1) was dissolved in 1 ml of methanolic 0.5% solution of $H_2SO_4$ (1 ml of diglyme) and 100 µl of 1 N HCl was added (alternatively, 50 µl trifluoroacetic acid may be used as well), the reaction mixture was put in an ampule that was then sealed and kept at 80° C. for 2 hr. After cooling, the ampule was opened, and the contents were dissolved in 5 ml of methylene chloride and washed in turn with water (3×5 ml) and saturated aqueous NaCl (50 ml), and then dried over anhydrous $Na_2SO_4$, filtered and stored at −80° C. The trimethylsilylether of methyl esters of 5-HETE and 5-HEPE were converted to their corresponding polyconjugated fatty acid methyl esters using similar protocols.

The yields of the conjugated tetraenoic acid methyl esters measured spectrophotometrically were 70–74% based on the parent trimethylsilylether of the methyl ester of the hydroxy acid. The isomer compositions determined by HPLC analysis after a 2 hr reaction time were the same as for the synthesis involving the use of excess DBU. There was a tendency for the amount of the all trans-isomers to increase with the reaction time.

Acidic cleavage of allylic lactone ring (FIG. 1, reaction (5)). To a solution of 350 mg of γ-lactone 4-HDHE in 3 ml of absolute methanol was added 2 ml of 0.5% of concentrated sulfuric acid in absolute methanol. The mixture was put in an ampule, sealed and kept at 80° C. for 1 hr. The reaction mixture changed from colorless to yellow. After cooling, the ampule was opened and the reaction contents diluted with 50 ml of water and 50 ml of methylene chloride. The organic layer was separated and the aqueous layer extracted with methylene chloride (2×50 ml). The combined organic layers were washed sequentially with water (50 ml) and saturated aqueous NaCl (50 ml), dried over anhydrous $Na_2SO_4$, filtered and stored at −80° C. The yield determined spectrophotometrically was 85%. The resulting crude mixture of methyl esters of 4E,6E,8E,10Z,13Z,16Z,19Z-docosaheptaenoic acid (about 80%) and 4E,6E,8E,10E,13Z,16Z, 19Z-docosaheptaenoic acid (about 20%) was purified by HPLC and analyzed further (VIIc, FIG. 1). Similarly, from the δ-lactone of 5-HEPE, a mixture of 5E,7E,9E,11Z,14Z, 17Z-eicosahexaenoic (about 80%) and 5E,7E,9E,11E,14Z, 17Z-eicosahexaenoic (about 20%) acids (VIIb, FIG. 1) were synthesized with a total yield determined spectrophotometrically of 81%; from the 6-lactone of 5-HETE a mixture of 5E,7E,9E,11Z,14Z-eicosapentaenoic (about 80%) and 5E,7E,9E,11E,14Z-eicosapent (about 20%) acids (VIIa, FIG. 1) were synthesized with a total yield determined spectrophotometrically of 83%. Spectral data for these newly synthesized compounds were the same as those for the conjugated polyunsaturated fatty acids synthesized with the use of excess of DBU (as described above).

Synthesis of epoxides from iodolactones and epoxide ring opening to the corresponding isomeric bromoacetates (FIG. 1, reactions (3) and (4)). The methyl ester of 4,5-epoxy,7Z, 10Z,13Z,16Z,19Z-docosapentaenoic acid was synthesized as follows. To a solution of 9.7 g (21 mmol) of the γ-iodolactone of DHA (Ic, FIG. 1) in 50 ml of methanol was added 16 ml of triethylamine (11.6 g, 5.5 eq). The reaction mixture was refluxed for 3 hrs and then evaporated under vacuum. The residue was stirred with hexane (3×70 ml), filtered, evaporated under vacuum, and purified by column chromatography on 30 g of silica gel using a gradient of ether in hexane (0→10%). The yield was 5.40 g (71%.) of (Vc, FIG. 1) as a colorless, mobile oil with an $R_f$ approximately 0.58 (hexane-ether, 1:1). Mass spectrum: m/z (I%): $[M]^+$ 358 (3), $[M-MeO]^+$ 327 (8). $^1$H-NMR (CDCl$_3$, δ, ppm): 0.99 t (H-22; 3H), 1.86 m—(H-3; 2H), 2.40 m (H-6; 2H), 2,50 m (H-2; 2H), 2.84 m (H-9,12,15,18; 8H), 2.98 m—(H-4,5; 2H), 3.69 s—(COOCH$_3$, 3H), H-7,8,10,11,13, 14,16,17,19,20—5.37 m). Spectral data for this compound were in full agreement with those reported previously (Kuklev, D. V. et al. (1991) Bioorganicheskaya Khimiya 17(11):1574–1581; and Kuklev, D. V. et al. (1992). Phytochemistry 31:2401–2403).

The mixture of isomeric bromoacetates (VI) was synthesized as follows. To a solution of 305 mg of the methyl ester of 4,5-epoxy, 7Z,10Z,13Z,16Z,19Z-docosapentaenoic acid in 10 ml of dry ether was added a solution of 120 mg (1.15 eq) of acetylbromide in 10 ml of dry ether. The reaction mixture was kept at room temperature for one hour and then washed with water (3×20 ml) and saturated NaCl (25 ml) and dried over Na$_2$SO$_4$. The dry extract was filtered, evaporated under vacuum, and purified by column chromatography on 10 g of silica gel using a gradient of ether in hexane (0→30%). The yield was 355 mg (87%) as a colorless oil with $R_f$ approximately 0.65–0.8 (hexane-ether, 1:1). The properties of the compounds in good agreement with those reported earlier (Kuklev, D. V. et al. (1997) Chemistry and Physics of Lipids 85:125–134; and Kuklev, D. V. et al. (1996) Bioorganicheskaya Khimiya 22:622–627).

Reaction of the bromoacetates with DBU. Formation of tetraenoic conjugated fatty acids (FIG. 1, reaction (9)). To a solution of isomeric bromoacetates (V, FIG. 1) (200 mg) in 5 ml of dry benzene was added 200 μl (approximately 1.5 eq) of dry DBU. The reaction mixture was kept at room temperature for 96 hr. The yield of conjugated tetraene determined spectrophotometrically was 55%. The final reaction mixture was handled as for the synthesis of conjugated fatty acids from iodolactones (as described above) and stored in methanol at −60° C.

Synthesis of 4-methyl-1,2,4-triazoline-3,5-dione (MTAD) adducts from conjugated fatty acids for mass spectrometric analysis. The method was essentially the same as that described by Dobson (Dobson, G. (1998) J. Am. Oil Chem. Soc. 75:137–142). Briefly, to a solution of a conjugated fatty acid methyl ester of known concentration measured spectrophotometrically was added MTAD (1 mg/ml in dichloromethane) at a ratio of one mole per one conjugated fragment (i.e. two conjugated double bonds); for example, to 250 μl of 5E,7E,9E,11E,14Z,17Z-eicosahexaenoic acid (2.1 mg/ml in dichloromethane) was added 200 μl of MTAD (1 mg/ml) in dichloromethane. An aliquot of the reaction mixture was analyzed by GC-MS immediately after derivatization. The MTAD adducts are stable for months when stored at −80° C. in tightly closed vials.

Synthesis of oxazolines of conjugated fatty acids for mass spectrometric analysis. The method was essentially the same as reported recently (Kuklev, D. V., and W. L. Smith (2003) J. Lipid. Res. 44:1060–1066). Briefly, to a solution of 1 mg of a fatty acid or a mixture of fatty acids in 0.2 ml of tetrahydrofuran (THF) in a microvial (1–3 ml volume) was added 0.2 ml of a solution of 1 mg of triethylamine in THF. The reaction mixture was shaken vigorously and 1 mg of isobutylchloroformate in 0.2 ml of THF was added. The reaction mixture was maintained at room temperature for 30 min and then evaporated under a stream of nitrogen. The residue was dissolved in dry hexane (0.3 ml) and filtered through glass wool prewashed with hexane, and the clean filtrate was collected and evaporated under a stream of nitrogen. The dry oily residue of the purified mixed anhydride was dissolved in 0.3 ml of THF and 1 mg of ethanolamine in 0.2 ml of THF was added. After 15 min, the reaction mixture was evaporated under a stream of nitrogen, dissolved in 0.3–0.4 ml of trifluoroacetic anhydride, and transferred into a reaction vial equipped with tightly fitting lid. The vial was closed tightly, and the reaction mixture was kept at 45° C. for 30 min. The reaction mixture was cooled to room temperature and volatile materials evaporated under a stream of nitrogen. The dry oily residue of the oxazoline was dissolved in dry hexane (0.3 ml) and filtered through glass wool prewashed with hexane and then analyzed by GC-MS.

EXAMPLE 3

Reactions of Iodolactones with Excess of DBU

This example describes in more detail the formation of conjugated tetraenoic fatty acids by reaction of iodolactones with excess DBU, as the yields observed for these reactions were particularly high.

HPLC Analysis

Figure 2:
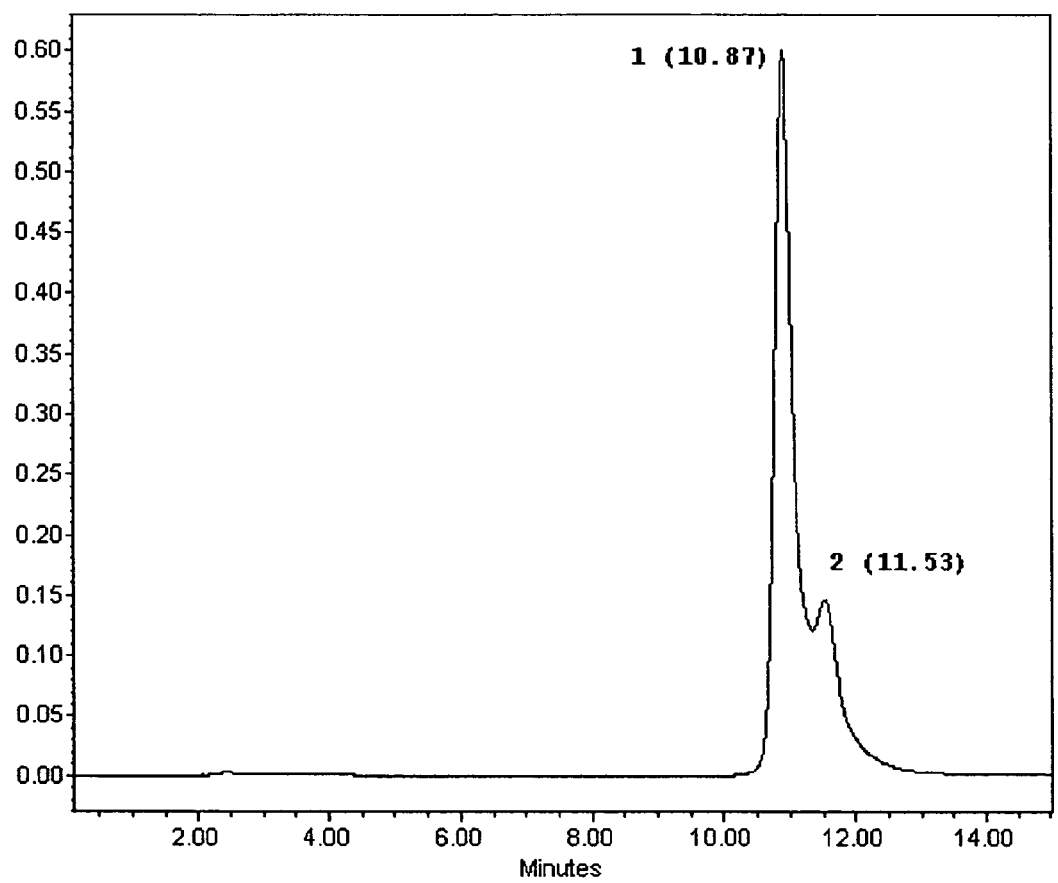
FIG. 2 shows the results of HPLC analysis of the reaction mixture of the conjugated fatty acids derived from eicosapentaenoic acid. Column: Nucleosil-C 18 (4.6×250, 5 µm), Mobile phase: MeOH:water:AcOH (85:15:0.1). Flow rate: 1.5 ml/min. Detection: at 300 mm.

In all of these reaction mixtures, two major peaks are present; these two peaks are designated Compound 1 and Compound 2 in reference to the sequence of their elution from RP-HPLC (see FIG. 2). Thus, from HPLC analysis of the reaction mixture of δ-iodolactone of EPA treated by 2.2 equivalents of DBU for 72 hrs (as described above for Reaction 1, FIG. 1), two major peaks of the products are present, with $k'_1$=5.75 (10.87 min) and $k'_2$=6.16 (11.53 min), for Compound 1 and Compound 2, respectively. The difference in the retention times between the compounds is sufficient to separate them in preparative scale and of high purity (>95%).

The HPLC data on polyconjugated fatty acids derived from DHA and AA are described in Example 2.

UV Spectroscopy

Figure 3:
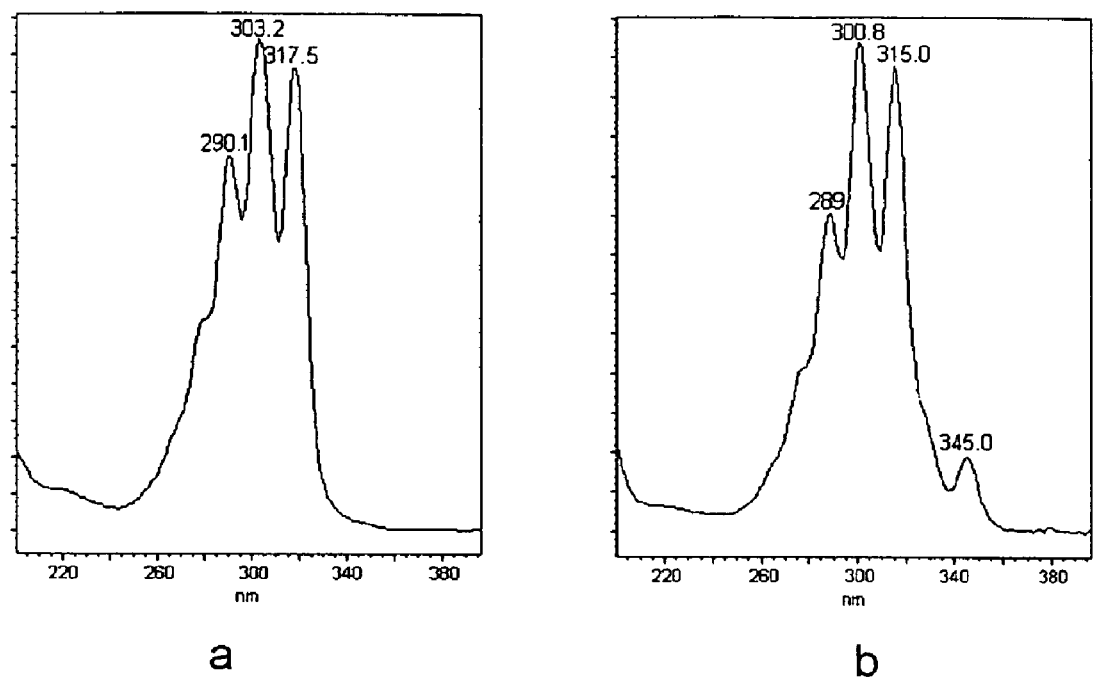
FIG. 3 shows the UV Spectra (in MeOH) of a) Compound 1 and b) Compound 2 derived from natural eicosapentaenoic acid.

UV spectra of the compounds separated by HPLC demonstrated the characteristic ultraviolet absorptions for a t,t,t,c tetraene functionality (λ=290.1, 303.2, 317.5 nm) in Compound 1, which were replaced in the absorption spectra of Compound 2 with those characteristic for a t, t, t, t-tetraene (λ=289, 300.8, 315 nm) (Hamberg, M. (1995) In Advances in Prostaglandin, Thromboxane and Leukotriene Research (B. Samuelson, Paoletti, R., Ramwell, P., editors; Raven Press, New York), pp. 193–198). These UV-spectra are shown on FIG. 3.

The main difference between the spectra is the hypsochromic shift of the Compound 2 peak maxima of about 3 nm. On the basis of these preliminary observations, it was assumed early in the structure elucidation process that Compound 1 and Compound 2 were geometrical isomers of one another, due to the similarity in spectroscopic properties of the two molecules, HPLC mobility, and the spontaneous room temperature conversion of Compound 1 to Compound 2, that can be monitored by HPLC.

The UV-data on polyconjugated fatty acids derived from DHA and AA are described in Example 2.

Fluorescence

Figure 4:
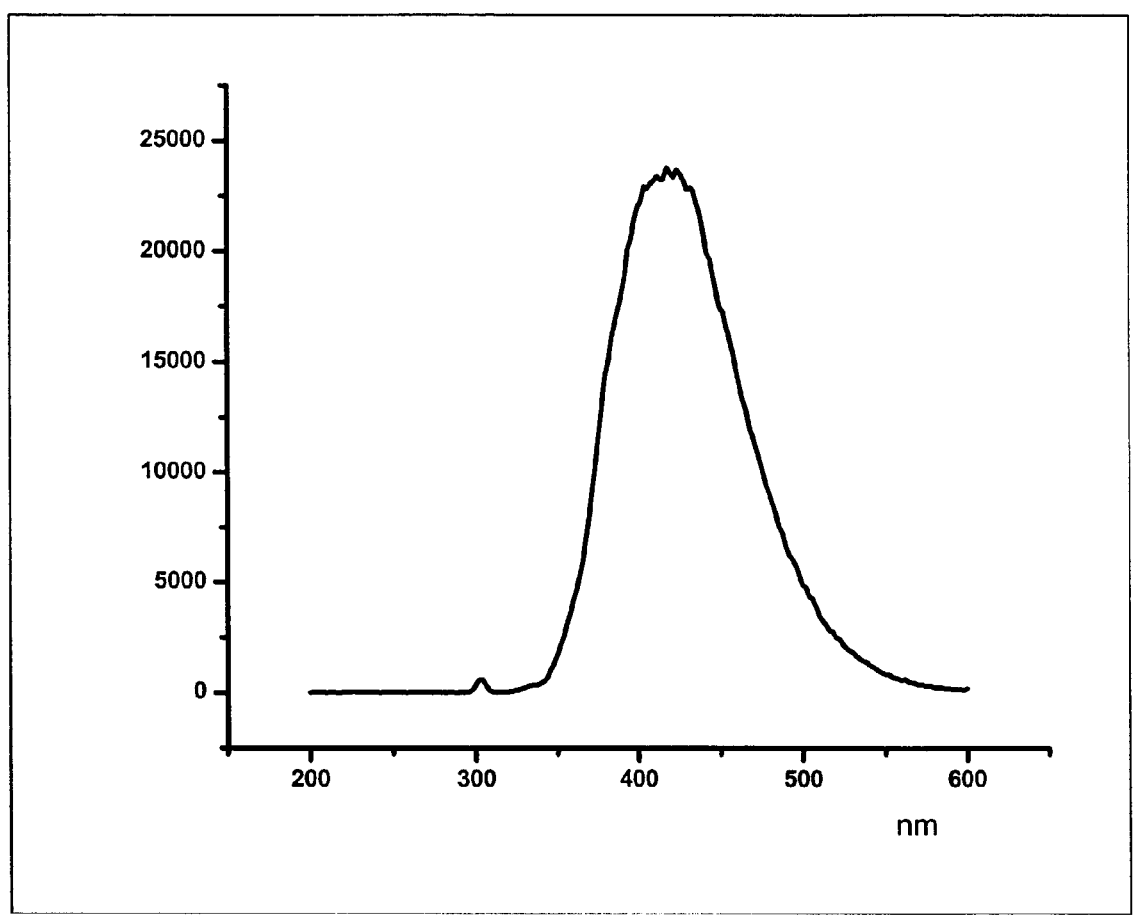
FIG. 4 shows fluorescence spectrum of Compound 1 derived from natural eicosapentaenoic acid. Ex $\lambda$=303 nm, Em $\lambda_{max}$=428 nm (in methanol).

The emission spectrum of Compound 1 derived from natural EPA in methanol at 23° C. is shown in FIG. 4. The emission origin is at about 350 nm, and a broad maximum (at about 422 nm for t,t,t,t- and 428 t,t,t,c-isomer) with little fine structure is observed. The emission spectrum is essentially independent of the particular solvent. The fluorescence quantum yield was determined as described previously (Sklar, L. A. et al. (1977) Biochemistry 16:813–819), and was consistent with that obtained for parinaric acid (Sklar, L. A. et al. (1977) Biochemistry 16:813–819).

The fluorescence data on polyconjugated fatty acids derived from DHA and AA are described in Example 2.

Mass Spectroscopy

As neither Compound 1 nor Compound 2 gave meaningful mass spectral information (electron impact, chemical ionization) when analyzed in the form of their methyl esters, the more stable Compound 2 was converted into the corresponding pyrrolidide under mild conditions (Kuklev, D. V., and V. V. Bezuglov (1994) Bioorganicheskaya Khimiya 20:341–366); however, it was insufficiently volatile, and the pirrolidide underwent on column degradation during GC-MS analysis. Better results were obtained when the acids were analyzed in the form of their oxazolines (Kuklev, D. V., and W. L. Smith (2003) J. Lipid. Res. 44:1060–1066). In the mass spectrum of the oxazoline of Compound 2 (the mass spectrum of Compound 1 was almost the same), a prominent molecular ion is present at m/z 325 (18%) and this is accompained by a peak at m/z 324 (14%). This suggests that the molecular mass of Compound 2 is two m.u. less than that of the starting EPA and correlates with the structure of Compound 2 being an eicosahexaenoic acid. The spectrum can be separated into two parts. The first part, located in the higher mass region, contains prominent ions at m/z 216 (17%), m/z 256 (20%), m/z 296 (8%) and m/z 310 (45%) that represent two methylene interrupted double bonds in the ω3 position (i.e. fragments $[M-CH_3]^+$ at m/z 310, and $[M-CH_2CH_3]^+$ at m/z 296). The second part of the spectrum, in the lower mass region with the m/z below 216, represents a very complicated fragmentation of the molecule at sites of conjugation. Nonetheless, prominent peaks are clearly seen for ions at m/z 85 (100%), 98 (65%), 138 (94%) (Δ5 double bond). Therefore, the normal fragmentation of an oxazoline peculiar to fatty acids having methylene interrupted double bond systems terminates at C-12, but starts, as anticipated, for non-conjugated fatty acids with C5, which indicates that the position of the conjugated system of double bonds between C5–C12 in Compond 2.

Figure 5:
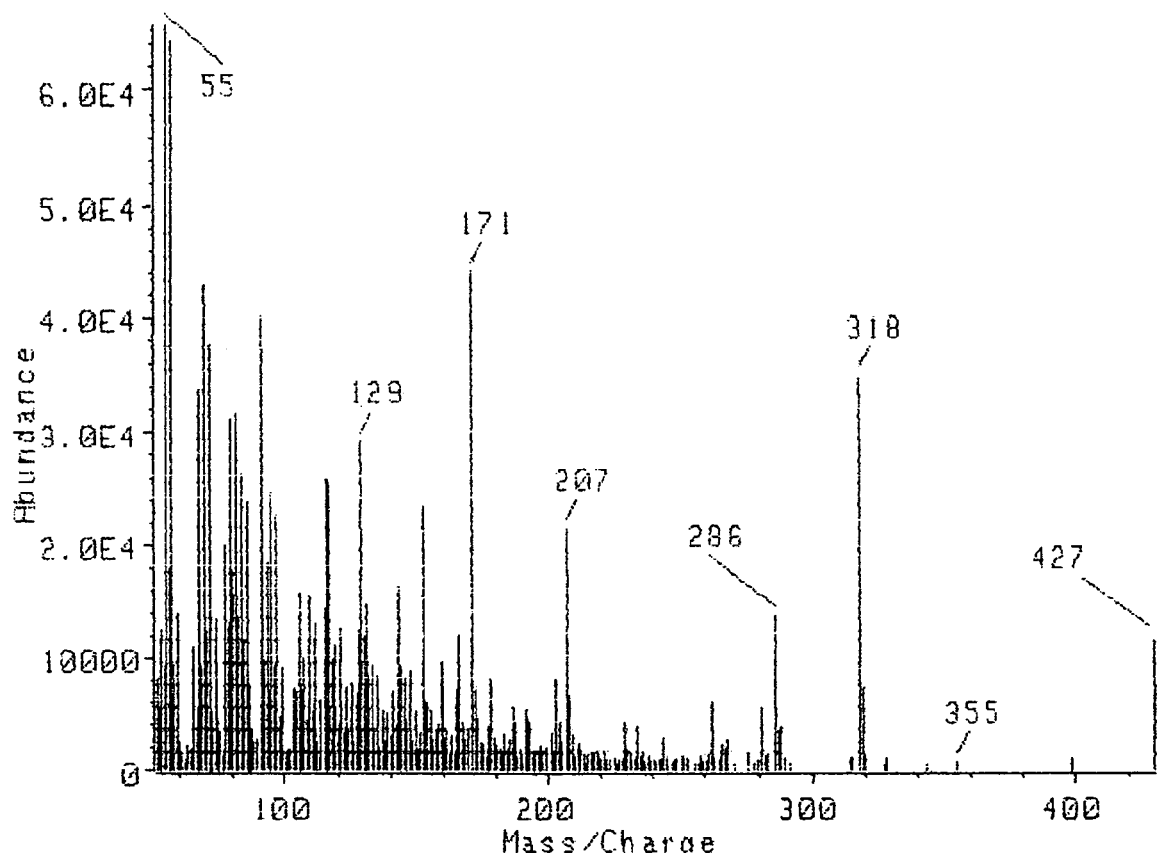
FIG. 5 shows a mass spectrum of C9-C 12 isomer of MTAD adduct with compound 2 derived from natural eicosapentaenoic acid. Molecular m/z 427 and diagnostic m/z 318 ions are clearly seen.

To confirm the position of the conjugated system of double bonds, the MTAD (4-methyl-1,2,4-triazoline-3,5-dione) adduct of Compound 2 was analysed by GC-MS using the technique developed by Young (Young, D. C. et al. (1990) J. Chromatogr. 522:295–302) and applied by Dobson (Dobson, G. (1998). J. Am. Oil Chem. Soc. 75:137–142) to dienoic and trienoic conjugated fatty acids and by us to tetraenoic fatty acids (FIG. 5). The reaction between MTAD and these compounds is rapid, as indicated by the immediate discoloration of the reagent following its addition. MTAD reacted with conjugated tetraene to form at least three major 1:1 adducts, together with some amounts of products having the same spectra but different mobilities on gas chromatography—a problem of the method originally described by Dobson (22). That is, the reaction between Compound 2 and MTAD was as if as Compound 2 had three independent diene systems. All three regioisomers of the 1:1 adducts between MTAD and Compound 2 were detected, and all of them had a prominent molecular ion $[M]^+$ -m/z 427, ≈15%; and diagnostic ions of $[M-C_8H_{13}]^+$-m/z 318, 22% thus identifying the location of the ring adduct between C-9 and C-12 (and therefore a 9,11-diene system in Compound 2) (See FIG. 5); $[M-C_{10}H_{15}]^{3O}$-m/z 292, 17% as expected for an adduct ring located between C-7 and C-10 (and therefore a 7,9-diene system in Compound 2; $[M-C_{12}H_{17}]^+$-m/z 266, 20% and $[M-C_5H_9O_2]^+$-m/z 326, 8%—identi between C-5 and C-8 (and therefore a 5,7-diene system in Compound 2. Hence, in Compound 2 the conjugated tetraene group is located between C-5 and C-12, and thus, the double bonds are at positions C-5, C-07, C-9 and C-11.

The data on mass spectrometry of oxazolines and MTAD—adducts derived from polyconjugated fatty acids from DHA and AA are described in Example 2.

$^1$H-NMR Spectroscopy

Figure 6:
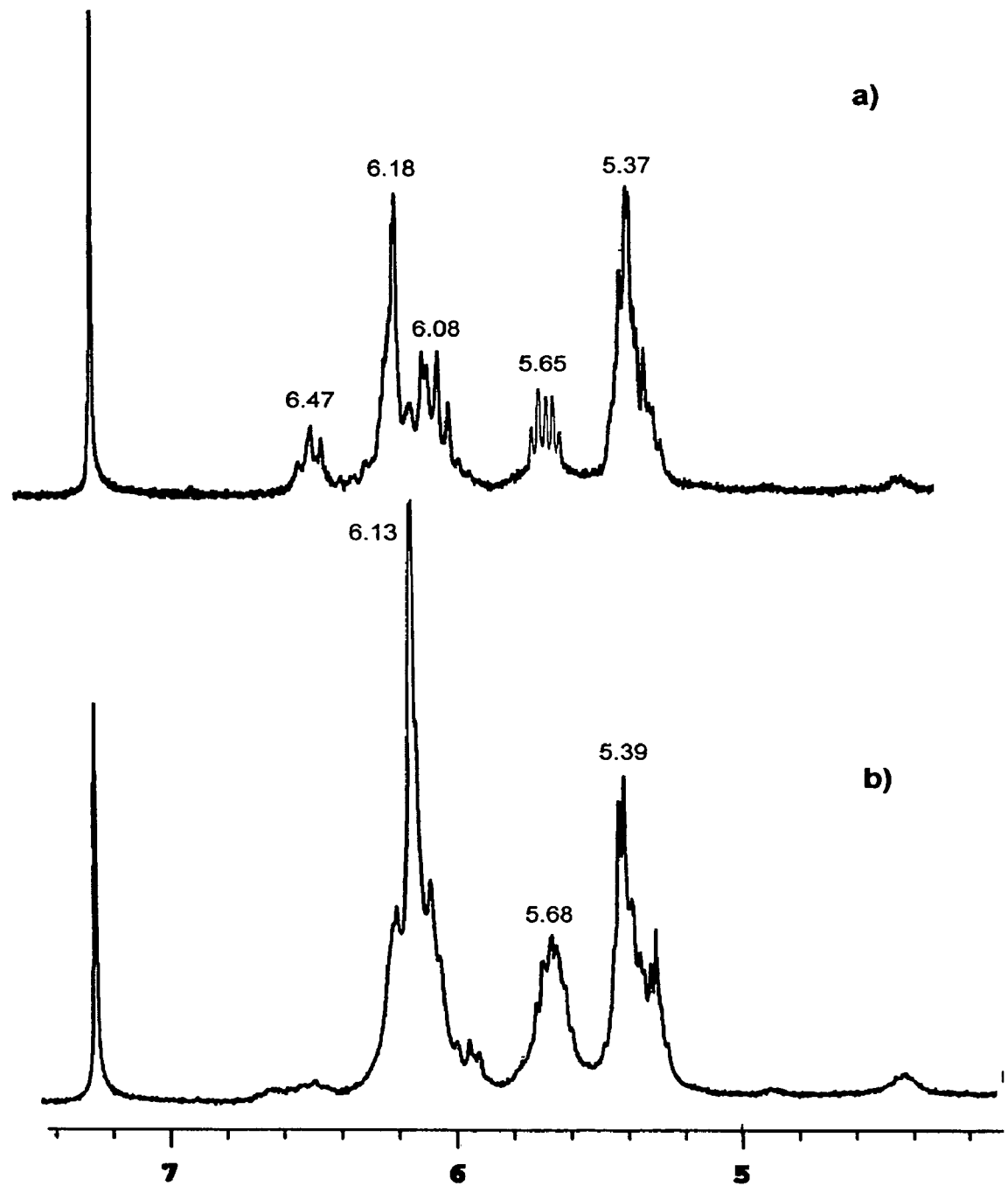
FIG. 6 shows low field fragments of $^1$H-NMR ($\delta$, ppm, CDCl$_3$, 300 MHz) spectra of a) Compound 1 and b) Compound 2.

The full data of $^1$H-NMR spectra, shown in FIG. 6, is summarized as follows:

Compound 1 synthesized from eicosapentaenoic acid: δ 0.96 (3H, t, J=7.5 Hz, H-20), 1.73 (2H, m, H-3), 2.06 (2H, m, H-19), 2.14 (2H, m, H-4), 2.35 (2H, t, 7.4, H-2), 2.80 (2H, m, H-16), 2.96 (2H, m, H-13), 5.37 (5H, m, H-12,14,15,17,18), 5.65 (1H, dt, $J_{5,6}$=14.4 Hz, $J_{54}$=6.9 Hz, H-5), 6.08 (1H, m, H-6), 6.18 (4H, m, H-7,8,9,11), 6.47 (1H, dd, $J_{10,9}$=13.7, $J_{10,11}$=11.1, H-10).

Compound 2 obtained from eicosapentaenoic acid: δ 0.95 (3H, t, J=7.6 Hz, H-20), 1.73 (2H, m, H-3), 2.05 (2H, m, $H_2$-19), 2.16 (2H, m, H-4), 2.35 (2H, t, 7.2, H-2), 2.76 (2H, m, H-16), 2.86 (2H, m, H-13), 5.39 (4H, m, H-14,15,17,18), 5.68 (2H, m, $J_{5,6}$≈$J_{11,12}$=14.5, $J_{5,4}$≈$J_{12,13}$=7.1, H-5,12), 6.13 (6H, m, H-6,7,8,9,10,11).

From these data, it was determined that there were twelve olefinic methines, six aliphatic methylenes, one methyl group, and one carbonyl carbon in both compounds. Two of the methylenes were bisallylic groups (as indicated by their chemical shifts, one at δ2.80 and another at δ2.96). Selective decoupling experiments demonstrated coupling from the C2-methylene at δ2.35 through the aliphatic protons at δ1.73 ppm (C3) to the δ2.14 (C4) and further to the olefinic proton at approximately δ5.6 at C5. Similarly, coupling from the terminal methyl at δ0.96 through the methylene protons at δ2.06 (C19) to the cluster of olefinic protons at δ5.3–5.4 established that part of the molecule. The relative positions in the conjugated tetraene functionality of the eight low-field proton signals in Compound 1 at δ5.65 (1H), δ 6.08 (2H), δ6.18 (4H), and δ6.47 (1H) were assigned authentically on the basis of selective decoupling experiments and supported by comparison with $^1$H-NMR spectra of Compound 2 where eight low-field proton signals formed two clusters at δ5.7 (2H, H-5,H-12) and at δ 6.13 (6H, H6-H11). Additional support of this assignment was provided by comparison of the observed chemical shifts and coupling constants with those revealed in experiments with natural conjugated fatty acids (Lopez A. and Gerwick W. H. (1987) Lipids Vol. 22, No. 3, pp. 190–194; Michailova M. V. et al. (1995) Lipids 30 (7): 583–589; and Wise M. L. et al. (1994) Biochemistry 33: 15223–15232).

The configuration of the conjugated double bonds in Compound 1 can be seen from the data presented; thus, the doublet of doublets at δ6.47 (H-10) with the couple constants (13.7 Hz and 11.1 Hz) is a very common signal for a methyne proton in the third position to the edge of a conjugated system of double bonds if the terminal double bond (C11–C12) has cis-configuration and the second double bond has trans one (C9-C10) (Michailova M. V. et al. (1995) Lipids 30 (7): 583–589; and Wise M. L. et al. (1994) Biochemistry 33: 15223–15232). One more diagnostic signal is the nicely resolved doublet of triplets at δ5.73, which is well known for terminal methyne at trans double bond in a conjugated system (Wise M. L. et al. (1994) Biochemistry 33: 15223–15232). Isomerisation of Compound 1 to Compound 2 results in the disappearance of the well shaped signals at δ5.73 and δ6.47, and in the formation of only two signal clusters at 6.1 (6H) and 5.7 (2H). The coupling constants of external methynes were almost the same with the values in 14.5 Hz (trans double bond) and 7.1 Hz (aliphatic methylene). These data are in excellent agreement with the structures of 5E,7E,9E,11Z-system of conjugated element for Compound 1 derived from EPA and AA (4E, 6E,8E,10Z derived from DHA), and 5E,7E,9E,11E-system of conjugated element for Compound 2 derived from EPA and AA (4E,6E,8E,10E derived from DHA).

The data on $^1$H-NMR analysis of polyconjugated fatty acids from DHA and AA are described in Example 2.

Structure Assignments

Thus, the results of HPLC, UV, Fluorescence spectroscopy, $^1$H-NMR, and GC-MS of derivatives supported the assignments of the following structures (shown in FIG. 7) for compounds derived from arachidonic acid:

Compound 1: 5E,7E,9E,11Z,14Z-eicosapentaenoic acid (FIG. 7, structure A); and

Figure 7:
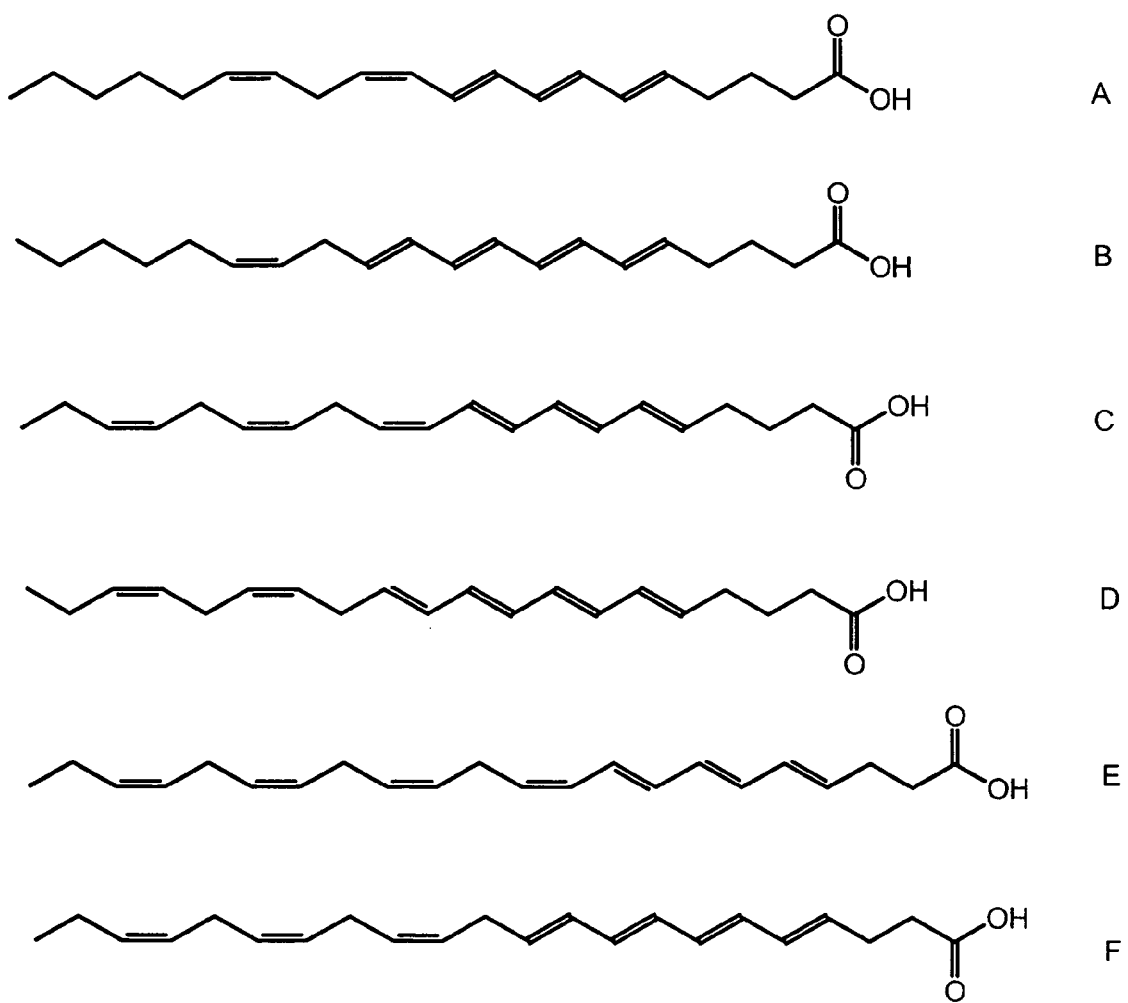
FIG. 7 shows structures of polyconjugated and polyunsaturated fatty acids synthesized.

Compound 2: 5E,7E,9E,11E,14Z-eicosapentaenoic acid (FIG. 7, structure B).

Similarly, for compounds derived from eicosapentaenoic acid, the following assignments were made:

Compound 1: 5E,7E,9E,11Z,14Z,17Z-eicosahexaenoic acid (FIG. 7, structure C); and Compound 2: 5E,7E,9E,11E,14Z,17Z-eicosahexaenoic acid (FIG. 7, structure D).

Similarly, for compounds derived from docosahexaenoic acid, the following assignments were made:

Compound 1: 4E,6E,8E,10Z,13Z,16Z,19Z-docosaheptaenoic acid (FIG. 7, structure E);

and Compound 2: 4E,6E,8E,10E,13Z,16Z,19Z-docosaheptaenoic acid (FIG. 7, structure F).

EXAMPLE 4

Synthesis of Parinaric Acid Derivatives

This Example describes the synthesis of parinaric acid derivatives using a method of one embodiment of the present invention.

A. Materials and Methods

Materials. 1,8-diazabicyclo[5.4.0]undec-7-ene (DBU), acetyl chloride and urea were purchased from Sigma Chemical Co. (St. Louis, Mo.). Flax Oil (57% α-linolenic acid) was purchased from Walmart. Trifluoroacetic anhydride, ethanolamine, isobutylchloroformate, pyridine, pyrrolidine and 4-methyl-1,2,4-triazoline-3,5-dione were products of Aldrich Chemical Co. (Milwaukee, Wis.) with a purity of 96%. Benzene, hexane, ether, acetonitrile were distilled over phosphorus pentoxide; triethylamine, tetrahydrofuran (THF), and methanol were distilled over metallic sodium before use. DBU was distilled over CaH$_2$ in vacuo. Silica gel "Selecto" 32–63 mm was purchased from Selecto Scientific (Georgia, USA). TLC plates were purchased from Sigma Chemical Co. A 5% solution of phosphomolybdic acid in methanol spray and heating of the TLC plates for 2–3 min on a hot plate (ca. 100° C.) was used to visualize products.

Equipment. All mass spectra were recorded on a Hewlett-Packard 5890 gas chromatograph combined with Hewlett-Packard 5970 series mass selective detector operated with a Hewlett-Packard 7946 computer. Gas chromatography conditions for GC-MS were as follows: He was used as the carrier gas at a flow rate of m/sec, the oven temperature was maintained at 210° C., the injector temperature was 250° C. and the interface temperature was 250° C. GC analysis was performed with the use of a capillary column DB-5 ms (30 m×0.32 mm, 1 mkm) (J&W, USA); the injector split ratio was kept constant at 1:60. Mass detector conditions were as follows: electron energy 70 eV, emission current 0.8 mA, accelerating voltage 8 kV, scale from 50 to 1000. GC of fatty acids was performed on a Shimadzu GC-17A3 gas chromatograph, equipped with Restek Stabilwax (30 m×0.32× 0.25 μm) or with Restek Rtx-5 (15 m×0.25 mm×0.25 μm) columns, a flame ionization detector and He as the carrier gas. HPLC analysis and preparative separations were performed on a Shimadzu LC-10 HPLC system equipped with a Shimadzu SPD-M10AVP photodiode array detector. Analytical RP-HPLC was performed on a Nucleosil-C18 analytical column (4.6×250 mm, 5 mm) (Xpertek, USA). Preparative separations were performed on a Kromasil C18 column (10×250, 5 mm) (Xpertek, USA). $^1$H-NMR spectra were recorded on an INOVA-300 (Varian, USA) operated at 300 Mhz. Samples were dissolved in CDCl$_3$ and tetramethylsilane used as an internal standard. All the signal assignments were performed based on selective decoupling experiments. All UV-Vis spectra were recorded on a Hewlett-Packard 8453 UV-Vis spectrophotometer operated with ChemStation data processing software.

Preparation of Br$_2$ solution. The bromine solution was prepared by saturating methanol with NaBr (about 65 g per 500 ml), filtering and adding then 10.1 g of liquid bromine with stirring to get a 0.1 M solution of the reagent.

Preparation of flax oil free fatty acids. Flax oil (500 g) was dissolved in a boiling ethanolic solution of potassium hydroxide (120 g of KOH in 1000 ml of ethanol) and boiled under reflux for 30 min. Water (500 ml) was added to the boiling reaction mixture, and it was boiled for an additional 30 min; after that, one more part of cool water (300 ml) was added and the reaction mixture was acidified with 5 N HCl to pH 5 and 500 ml of hexane was added to the warm solution. The organic layer was separated and washed sequentially with water (2×500 ml) and saturated aqueous NaCl (200 ml), dried over anhydrous Na$_2$SO$_4$ and evaporated in vacuo to form 410 g of flax oil free fatty acids with ALA concentration of 55% according to GC analysis.

Preparation of an ALA concentrate from flax oil fatty acids. The mixture of free fatty acids from flax oil was subjected to crystallization with urea to produce a mixture of fatty acids enriched in ALA. To a clear hot solution of 640 g of analytical grade urea in 1600 ml methanol a portion of the 400 g of the fatty acids of flax oil were dissolved with stirring. The mixture was allowed to cool slowly to room temperature for about four hr and then placed overnight at 0° C. The precipitate of urea complexes was filtered with suction, the filtrate evaporated to dryness, and warm water (200 ml) was added to the residue to dissolve the excess urea. The filtrate acids were isolated by separation on separatory funnel, and the lower layer was extracted with hexane (200 ml). The combined layers were washed by washed with warm water (40° C., 3×200 ml) and saturated aqueous NaCl (200 ml), and then dried over anhydrous $Na_2SO_4$ and evaporated in vacuum to yield 191 g of an ALA concentrate as a dark yellow oil 82% ALA, 18% linoleic acid as determined by GC analysis; the recovery of ALA was 68%.

Bromination of the ALA concentrate. To the solution of 10.0 g of the ALA concentrate in 500 ml of methanol, was added dropwise with rigorous stirring over 30 minutes a solution of 0.1N of bromine reagent (310 ml, 1.1 eq). Then 100 ml of 1% solution of HCl in methanol (prepared immediately before use by dissolving acetyl chloride in methanol) was added to the reaction mixture, which was then kept for 2 hr at room temperature. The reaction mixture was evaporated in vacuum, the dry residue was dissolved in 100 ml of water and extracted with ethyl ether (3×100 ml), washed with saturated aqueous NaCl (100 ml), dried over anhydrous $Na_2SO_4$ and evaporated under vacuum. The resulting mixture of bromides and unreacted ALA (14% as determined by GC) was used without additional purification.

Figure 9:
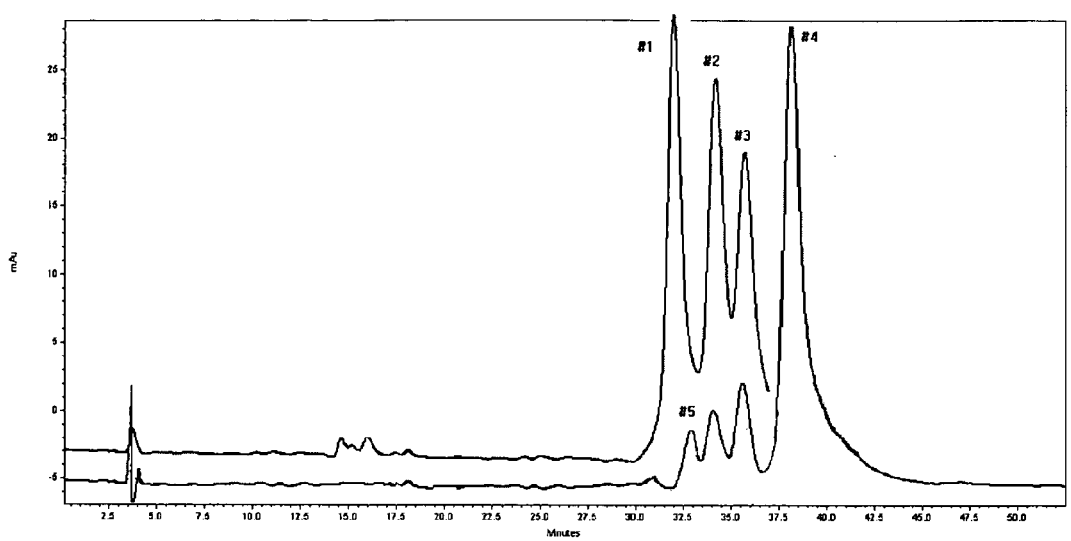
FIG. 9 shows HPLC analysis of reaction mixtures of α-parinaric acid (upper trace) and β-parinaric acid (lower trace).

Dehydrobromination of ALA bromides. DBU (12.2 ml; 1.15 eq) was added to the solution of the bromides obtained in the previous step in 100 ml of dry benzene with stirring. The reaction mixture was kept under nitrogen with stirring overnight. The yield of the target conjugated fatty acids was 65% as determined spectrophotometrically using an extinction coefficient for conjugated tetraenes $\epsilon 302=70,000$ 1 $mol^{-1}$ $cm^{-1}$. The reaction mixture was filtered, the filtrate evaporated in vacuo and the dry residue was stirred with 200 ml of hexane; the dissolved materials separated from a dark oily deposit and the hexane solution was washed with 2N HCl (2×200 ml), water (2×200 ml), saturated aqueous NaCl (200 ml) and dried over anhydrous $Na_2SO_4$. The HPLC chromatogram of the processed reaction mixture is shown in FIG. 9 (upper trace).

Figure 8:
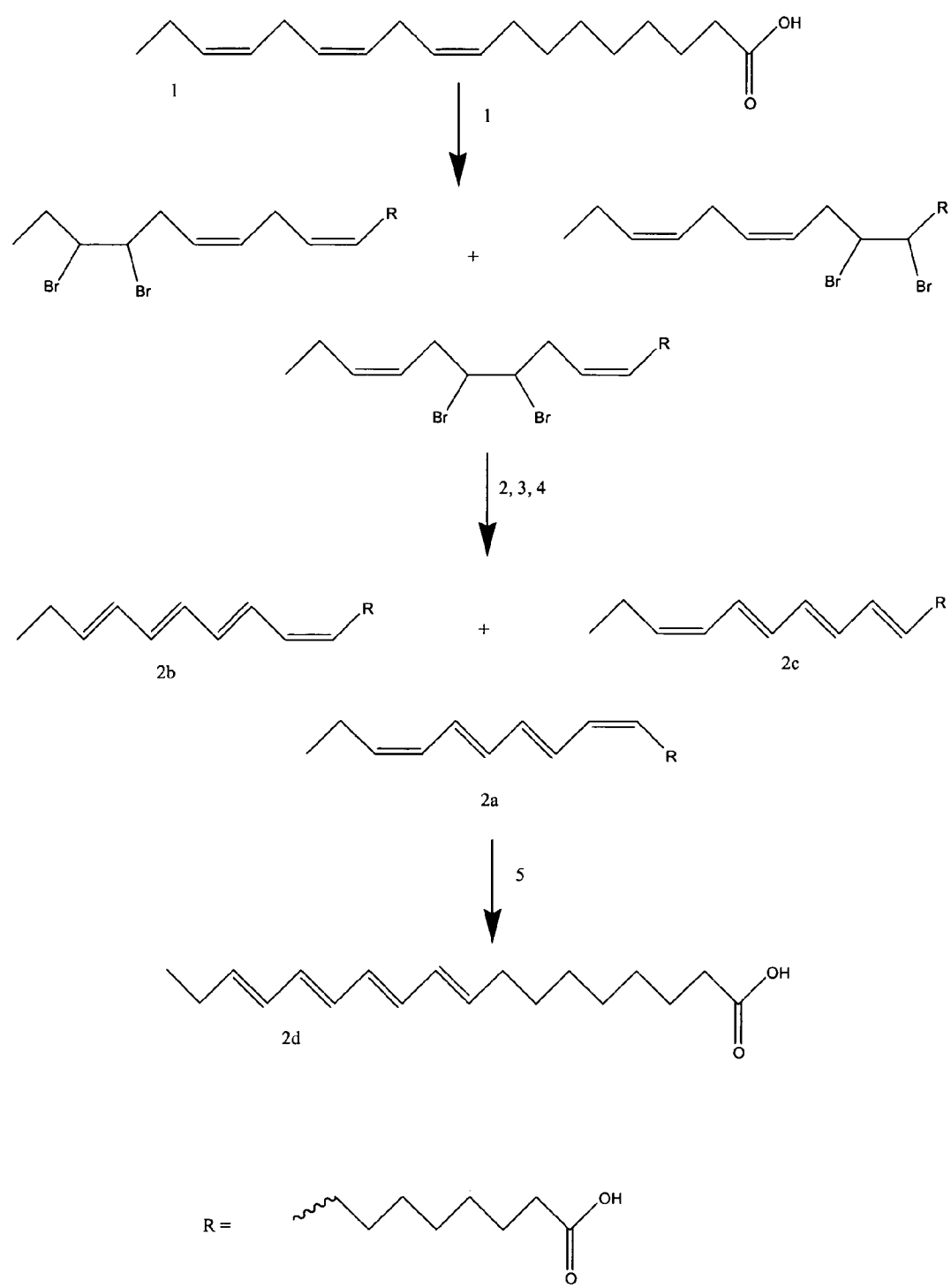
FIG. 8 shows a schematic synthetic scheme for the synthesis of parinaric acids (2a–d) from α-linolenic acid (1).

Isolation of α-parinaric acid and its two isomers. The dry extract obtained in the previous step was filtered, evaporated, dissolved in 200 ml of ethanol and combined with 20 ml of a 10% solution of KOH (1.1 eq) with stirring. After 16 hr at room temperature, the reaction mixture was acidified with 2 N HCl to pH 5 and extracted with ethyl ether (2×200 ml). The combined ether layers were washed with water (500 ml) and saturated aqueous NaCl (200 ml), dried over anhydrous $Na_2SO_4$ and evaporated under vacuum. The dry oily residue was crystallized at −60° C. three times from 100 ml of hexane. The light crystalline precipitate of the mixture of conjugated parinaric acids was separated by preparative HPLC. Preparative HPLC separation was performed using a KROMASIL column (250×10 mm, C18, 5 mm) with methanol-water-acetic acid (85:15:0.3) at a flow rate of 5 ml/min.

α-Parinaric acid (2a; FIG. 8); peak #1 (methyl ester) (FIG. 9). GLC (41%, ECL=19.23, Rtx 5). HPLC: k'=6.1 (methanol:$H_2O$:acetic acid; 85:15:0.3). UV: $\lambda_{max}$ (methanol) =291, 304 ($\epsilon$=70,000 1 $mol^{-1}$ $cm^{-1}$ and 319); MS, EI, methyl ester of 2a, m/z (I%): 290 (14%, M$^+$), 261 (4%, M$^+$-Et), 259 (4%, M$^+$-OMe), 161 (11%), 147 (20%), 133 (31%), 119 (38%), 105 (70%), 91(100%), 79 (75%), 55 (42%). $^1$H-NMR ($\delta$, ppm, 300 MHz, $CDCl_3$): 0.99 (t, 3H, $J_{18,17}$ 7.5, H-18), 1.28 (m, 8H, H-4,5,6,7), 1.59 (m, 2H, H-3), 2.1 (dq, 2H, $J_{17,16}$ 7.2, $J_{17,18}$ 7.5, H-17), 2.2 (m, 2H, H-8), 2.28 (t, 2H, $J_{2,3}$ 7.5), 5.38 (m, 2H, $J_{9,8}$ 7, $J_{16,17}$ 7.2, $J_{16,15}$ 10.0, H-9,H-16), 6.01 (dd, 1H, $J_{15,16}$ 10.0, $J_{15,14}$ 11, H-15), 6.17 (m, 4H, H-10,11, 12,13), 6.48 (m, 2H, $J_{14,15}$=$J_{11,10}$ 11, $J_{14,13}$=$J_{11,12}$ 14.5, H-11,14).

9Z,11E,13E,15E-)Octadecatetraenoic acid (2b; FIG. 8), peak #2 (methyl ester) (FIG. 9). GLC (33%, ECL=19.34 Rtx 5). HPLC: k'=6.6 (methanol:$H_2O$:acetic acid; AcOH; 85:15: 0.3). UV: $\lambda_{max}$ (methanol)=289, 302 ($\epsilon$=71,000 1 $mol^{-1}$ $cm^{-1}$ and 316); MS, EI, methyl ester of 2b, m/z (I%): 290 (17%, M$^+$), 261 (5%, M$^+$-Et), 259 (5%, M$^+$-OMe), 161 (13%), 147 (22%), 133 (33%), 119 (41%), 105 (73%), 91 (100%). $^1$H-NMR ($\delta$, ppm, 300 MHz, $CDCl_3$): 0.99 (t, 3H, $J_{18,17}$ 7.5, H-18), 1.28 (m, 8H, H-4,5,6,7), 1.59 (m, 2H, H-3), 2.1 (dq, 2H, $J_{17,16}$ 7.2, $J_{17,18}$ 7.5, H-17), 2.2 (m, 2H, H-8), 2.28 (t, 2H, $J_{2,3}$ 7.5), 5.36 (dt, 1H $J_{9,8}$ 7.2, $J_{9,10}$ 10.0, H-9), 5.73 (dt, 1H, $J_{9,8}$ 7, $J_{9,10}$ 10, H-16), 6.04 (dd, 1H, $J_{10,9}$ 10.0, $J_{10,11}$ 11, H-10), 6.2 (m, 4H, H-12,13,14,15), 6.43 (m, 1H, $J_{11,10}$ 11, $J_{11,12}$ 14.4, H-11).

9E,11E,13E,15Z-Octadecatetraenoic acid (2c; FIG. 8), peak #3 (methyl ester) (FIG. 9). GLC (27%, ECL=19.53 Rtx 5). HPLC: k'=6.9 (methanol:$H_2O$:acetic acid; 85:15:0.3). UV: $\lambda_{max}$ (methanol)=289, 302 ($\epsilon$=71,000 1 $mol^{-1}$ $cm^{-1}$ and 316); MS, EI, methyl ester of 2c: the same as for 2b. $^1$H-NMR ($\delta$, ppm, 300 MHz, $CDCl_3$): 0.99 (t, 3H, $J_{18,17}$ 7.5, H-18), 1.28 (m, 8H, H-4,5,6,7), 1.59 (m, 2H, H-3), 2.1 (dq, 2H, $J_{17,16}$ 7.2, $J_{17,18}$ 7.5, H-17), 2.2 (m, 2H, H-8), 2.28 (t, 2H, $J_{2,3}$ 7.5), 5.36 (dt, 1H $J_{16,17}$ 7.2 $J_{16,15}$ 10.0, H-16), 5.73 (dt, 1H $J_{9,8}$ 7, $J_{9,10}$ 10, H-9), 6.04 (dd, 1H, $J_{15,16}$ 10.0, $J_{15,14}$ 11, H-15), 6.2 (m, 4H, H-10,11,12,13), 6.42 (m,1H, $J_{14,15}$ 11, $J_{14,13}$ 14.4, H-14).

Isolation of crude β-parinaric acid. The dry extract of the reaction mixture from the dehydrobromination reaction was filtered, evaporated, dissolved in 200 ml of ethanol and saponified using the technique described above for saponification of flax oil. The resulting fatty acids were crystallized from 100 ml hexane three times at −60° C. and β-parinaric acid was purified further by HPLC.

β-Parinaric acid (2d; FIG. 8); peak #4 (methyl ester) (FIG. 9). GLC (ECL=19.80, Rtx 5). HPLC: k'=7.3 (methanol: $H_2O$:acetic acid; 85:15:0.3). UV: $\lambda_{max}$ (methanol)=286, 299 ($\epsilon$=73,000 1 $mol^{-1}$ $cm^{-1}$) and 313 nm; MS, EI, methyl ester of 2d, m/z (I%): 290 (22%, M$^{+)}$, 261 (7%, M$^+$-Et), 259 (6%, M$^+$-OMe), 161 (14%), 147 (23%), 133 (40%), 119 (44%), 105 (70%), 91(100%). $^1$H-NMR ($\delta$, ppm, 300 MHz, $CDCl_3$): 0.99 (t, 3H, $J_{18,17}$ 7.5, H-18), 1.29 (m, 8H, H-4,5, 6,7), 1.60 (m, 2H, H-3), 2.1 (dq, 2H, $J_{17,16}$ 7.2, $J_{17,18}$ 7.5, H-17), 2.1 (m, 2H, H-8), 2.32 (t, 2H, $J_{2,3}$ 7.5, H-2), 5.7 (m, 2H, H-9, H-16), 6.08 (m, 6H, H-10,11,12,13,14,15).

B. Results

The synthesis of parinaric acid isomers (2a–d) involved brominating naturally occurring ALA with 1.1 eq of $NaBr_3$ and subsequent double dehydrobromination with DBU. The resulting reaction mixture was comprised of three major components—α-parinaric acid 2a—a well-known fluorescent reagent that had never been synthesized previously, and two rarely described isomers 2b and 2c. These latter compounds originated from "double E2 elimination with shift" rearrangement.

Regioisomerism of molecular bromine addition to double bonds of PUFA depends on several parameters and had not been investigated in detail. The results described herein establish that the bromination of a PUFA by 0.1M bromine in methanol saturated with sodium bromide at room temperature proceeds smoothly with up to 45% regioselectivity at the 12,13-double bond of ALA. Under these conditions, addition of 1.1 eq of bromine leads to conversion of about 83–88% of the parent ALA to bromides with about 12–17% of the starting ALA left intact (according to GC analysis). Free polyunsaturated fatty acids or their esters both can be brominated in high yields. Brominating polyunsaturated fatty acids with molecular bromine in organic solvents (ether, methylene chloride, chloroform, hexane or acetic acid) proceeds with the formation of by-products together with the target dibromides, but the dibromides are always the main products of the reaction.

Dehydrobromination of the dibromides occurs in high yields using DBU in dry benzene. However, it is essential before dehydrobromination to protect the fatty acid bromides by converting them to esters. Dehydrobromination of free fatty acids dibromides by DBU leads to formation of up to 80% by-products, possibly due to various polymerization reactions. Esterified bromides undergo dehydrodromination within 16 hr with yields of more than 80%; the yields of tetraenoic componds were 62–65% for the three stage synthesis (bromination, esterification, and dehydrobromination). The reaction mixture contains the parinaric fatty acid isomers $2a$–$2b$–$2c$ in a ratio of about 0.5:0.3:0.2 as determined by GC. Only traces of β-parinaric acid ($2d$) were detected.

Compounds $2a$–$2c$ are not stable to alkaline treatment at elevated temperatures and can be isomerized to the all trans β-parinaric acid in high yield. Thus, saponification of the methyl esters of compounds $2a$–$2c$ with a 10% molar excess of KOH at room temperature for 16 hr leads to decreasing amounts of the α-parinaric acids (from 45% to 35–40%) and corresponding increased in β-parinaric acid. Use of a 50% excess of KOH and boiling the reaction mixture under reflux for 2 hours leads to a practically complete transformation of all isomers of α-parinaric acid to β-parinaric acid; there are also minor components with absorption maxima at λ=299 nm, but with chromatography mobilities different then that of β-parinaric acid (peak #5, FIG. 9). The present invention is not limited to a particular mechanism. Indeed, an understanding of the mechanism is not necessary to practice the present invention. Nonetheless, it is contemplated that this involves migration of the system of four conjugated trans-only-double bonds along the carbon chain with the formation of regioisomers of β-parinaric acid. Migration of the conjugated system of double bonds along the chain was not observed if there is even one cis-double bond. Thus, it is contemplated that a cis-double bond in the system of conjugated double bond serves as an anchor preventing movement along the carbon chain.

The parinaric acids ($2a$,$2b$,$2c$ and $2d$) can be synthesized using the method described herein with common laboratory equipment in hundred milligram yields in high (>96%) purity. All spectral properties ($^1$H-NMR, mass spectra, UV) of compounds $2a$–$2d$ were in excellent agreement with those reported for the naturally occurring compounds (Hamberg, Chem. Soc. Perkin Trans. 1:3065 (1993). The approach described herein for the synthesis of conjugated PUFAs is applicable for the synthesis of sets of conjugated fatty acids such as the synthesis of ω-6 isomers of parinaric acid from γ-linolenic acid.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A composition comprising a polyconjugated fatty acid, wherein the polyconjugated fatty acid is selected from the group consisting of 5E,7E,9E,11Z,14Z- and 5E,7E,11E,14Z eicosapentaenoic acid, 5E,7E,9E,11Z,14Z,17Z- and 5E,7E, 9E,14E,17Z-eicosanexaenoic acid, and 4E,6E,8E,10Z,13Z, 16Z,19Z- and 4E,6E,8E,10E,13Z,16Z,19Z-docosaheptaenoic acid.

2. A composition comprising an ester of the polyconjugated fatty acid of claim 1.

3. The composition of claim 2, wherein the ester is selected from the group consisting of a methyl ester and an ethyl ester.

4. A composition comprising a lipid comprising at least one polyconjugated fatty acid, wherein the polyconjugated fatty acid is the polyconjugated fatty acid of claim 1.

5. The composition of claim 4, wherein the lipid is a glycerolipid.

6. The composition of claim 5, wherein the glycerolipid is a triglyceride, a diglyceride, a monoglyceride, a phospholipid, a lysophospholipid, a glycolipid, or a lysoglycolipid.

7. A method of synthesizing a polyconjugated fatty acid product, comprising:
   a. providing an iodolactone of a fatty acid dissolved in dry benzene, wherein the fatty acid is arachidonic, eicosapentaenoic, or eicosahexaenoic acid; and
   b. reacting the fatty acid iodolactone with dry DBU to generate a polyconjugated fatty acid product.

8. The method of claim 3, wherein the fatty acid iodolactone is reacted with a molar excess of dry DBU, forming a polyconjugated fatty acid product.

9. The method of claim 7, wherein the fatty acid iodolactone is reacted with an about equimolar amount of dry DBU, forming an allylic lactone of the fatty acid, and further comprising:
   c. reacting the allylic lactone of the fatty acid with a molar excess of DBU.

10. The method of claim 7, wherein the fatty acid iodolactone is reacted with an about equimolar amount of DBU, forming an allylic lactone of the fatty acid, and further comprising:
   c. reacting the allylic lactone of the fatty acid with base to form a hydroxy fatty acid product;
   d. reacting the hydroxy acid product with chlorotrimethylsilane to form a trimethylsilylether of the methyl ester of the hydroxy acid; and
   e. reacting the trimethylsilylether of the methyl ester of the hydroxy acid product with acid to form a methyl ester of a polyconjugated fatty acid product.

11. The method of claim 7, wherein the fatty acid iodolactone is reacted with an about equimolar amount of DBU, forming an allylic lactone of the fatty acid, and further comprising:
   c. reacting the allylic lactone of the fatty acid with acid to form a methyl ester of a polyconjugated fatty acid product.

12. The method of claim 7, further comprising the step of purifying said polyconjugated fatty acid product comprising the steps of:
   a. providing a polyconjugated fatty acid product in a solvent;
   b. adding a high boiling solvent;
   c. evaporating the solvent in which a polyconjugated fatty acid product is dissolved;

d. dissolving the residual polyconjugated fatty acid product in a water/alcohol/acid solution; and e. isolating the polyconjugated fatty acid product by solid phase extraction chromatography.

13. The method of claim 12, further comprising concentrating and purifying the polyconjugated fatty acid by HPLC.

14. The method of claim 13, further comprising crystallizing the polyconjugated fatty acid at very low temperatures.

15. The method of claim 12, wherein the polyconjugated fatty acid product is a polyconjugated fatty acid or an ester of a polyconjugated fatty acid.

16. The method of claim 12, wherein the high boiling solvent is dry diglyme, triglyme, tetraglyme or DMSO.

17. A method of synthesizing a polyconjugated fatty acid, comprising:

a. reacting a free fatty acid, wherein said free fatty acid is alpha-linolenic acid, with bromine to produce a vicinal-dibromide of said alpha-linolenic acid; and b. reacting said vicinal-dibromide with DBU to generate parinaric acid isomers.

18. The method of claim 17, wherein said free fatty acid is derived from an oil by a method comprising the steps of a) dissolving said oil in a boiling ethanolic solution of potassium hydroxide to generate a reaction solution;

b) boiling said reaction solution under reflex;

c) acidifying said reaction solution;

d) extracting the organic layer from said reaction solution; and e) drying said organic layer to generate free fatty acids.

19. The method of claim 18, further comprising the step of enriching said free fatty acids for alpha-linolenic acid.

20. The method of claim 17, further comprising the step of purifying said parinaric acid isomers.

* * * * *